United States Patent
Srinivasan et al.

(10) Patent No.: US 12,020,816 B2
(45) Date of Patent: Jun. 25, 2024

(54) MACHINE LEARNING AUGMENTED SYSTEM FOR MEDICAL EPISODE IDENTIFICATION AND REPORTING

(71) Applicant: Merative US L.P., Ann Arbor, MI (US)

(72) Inventors: Raman Srinivasan, Plano, TX (US); Ajay Ashok Deshpande, Pleasantville, NY (US)

(*) Notice: Subject to any disclaimer, the term of this patent is extended or adjusted under 35 U.S.C. 154(b) by 482 days.

(21) Appl. No.: 17/483,895

(22) Filed: Sep. 24, 2021

(65) Prior Publication Data
US 2023/0103143 A1 Mar. 30, 2023

(51) Int. Cl.
*G16H 50/20* (2018.01)
*G06F 16/28* (2019.01)
*G16H 10/60* (2018.01)

(52) U.S. Cl.
CPC ............ *G16H 50/20* (2018.01); *G06F 16/283* (2019.01); *G16H 10/60* (2018.01)

(58) Field of Classification Search
CPC ........ G16H 50/20; G16H 10/60; G16H 20/10; G16H 15/00; G16H 20/00; G16H 50/70; G06F 16/283; G06F 16/35; G06F 16/3347; G06N 20/00; G06N 3/088
See application file for complete search history.

(56) References Cited

U.S. PATENT DOCUMENTS

| 8,700,433 B2 | 4/2014 | Dang |
| 10,923,233 B1 | 2/2021 | Wang et al. |
| 2008/0270120 A1* | 10/2008 | Pestian .................. G16H 40/20 705/2 |
| 2014/0249848 A1 | 9/2014 | Averill et al. |

(Continued)

FOREIGN PATENT DOCUMENTS

CN 106484674 A * 3/2017 ............. G06F 19/32

(Continued)

OTHER PUBLICATIONS

Gehrmann, Sebastian et al. "Comparing deep learning and concept extraction based methods for patient phenotyping from clinical narratives." PLoS ONE 13.2: e0192360. Public Library of Science. (Feb. 15, 2018) (Year: 2018).*

(Continued)

*Primary Examiner* — Linh Giang Le
(74) *Attorney, Agent, or Firm* — Stephen J. Walder, Jr.

(57) ABSTRACT

A medical episode analysis engine is provided. The engine generates a first matrix data structure having an entry for each concept pairing and storing a value representing relatedness weighted according to a temporal weighting function. The engine generates a second matrix data structure by calculating, for each entry in the first matrix, a relatedness measure of the concepts in the concept pairing based on a frequency of occurrence together. The engine generates, for each first concept, a concept embedding, based on the second matrix, that specifies, for each other second concept, a temporally weighted relatedness measure. The engine generates, for each anchor concepts, a corresponding episode definition comprising a plurality of related concepts corresponding to a same episode, based on the concept embedding. The engine processes new input data based on the episode definition data structures to identify instances of corresponding episodes in the new input data.

20 Claims, 10 Drawing Sheets

(56) References Cited

U.S. PATENT DOCUMENTS

2019/0005410 A1    1/2019    Shekhar et al.
2020/0243199 A1*    7/2020    Farley .................... G16H 70/20
2020/0251204 A1    8/2020    Teodoro et al.

OTHER PUBLICATIONS

"Clinical Classifications Software (CCS) for ICD-10-PCS (beta version)", Agency for Healthcare Research and Quality, Last Modified Nov. 5, 2019, 4 pages.

"Clinical Classifications Software Refined (CCSR)", Agency for Healthcare Research and Quality, Last Modified Mar. 5, 2021, 1 page.

"Current Procedural Terminology", Wikipedia, Last Edited May 6, 2021, 8 pages.

"Episode Groupers, Key Considerations for Implementing Clinical Episode Models", Health Care Transformation Task Force, Jan. 2019, 15 pages.

"Evaluating Episode Groupers: A Report from the National Quality Forum", The National Quality Forum, Sep. 5, 2014, 35 pages.

"Silhouette (clustering)", Wikipedia, Last Edited on Jul. 12, 2021, 3 pages.

"The Medical Episode Grouper: Applications and methodology", International Business Machines Corporation, IBM Watson Health, Apr. 2018, 7 pages.

Anonymous, "OptCare—A system for for personalizing clinical care pathways", IP.com Prior Art Database Technical Disclosure, IP.com No. IPCOM000244979D, Feb. 4, 2016, 13 pages.

Jurafsky, Dan et al., "Vector Semantics", Stanford University, accessed online Sep. 20, 2021, 90 pages.

Mathews, Peter et al., "SMERC: Social media event response clustering using textual and temporal information", 2018 IEEE International Conference on Big Data , pp. 3695-3700, 2018, submitted version arXiv:1811.05063v1 [cs.SI], Nov. 13, 2018, 8 pages.

Vink, Ritchie, "Algorithm Breakdown: Affinity Propagation", Ritchie Vink Blog, May 18, 2018, 12 pages.

\* cited by examiner

| OSTEOARTHRITIS | AMBULANCE TRANSPORTATION | BARIATRIC SURGERY PROCEDURES | ACUTE MYOCARDIAL INFARCTION |
|---|---|---|---|
| 1. Other Aftercare encounter<br>2. MAJOR JOINT REPLACEMENT OR REATTACHMENT OF LOWER EXTREMITY WITHOUT MCC<br>3. Anesthesia – knee and popliteal area<br>4. Surgical Procedures on the Femur (Thigh Region) and Knee Joint<br>5. Implant, device, or graft related encounter – knee<br>6. Medical Services – physical medicine and rehabilitation<br>7. Arthroplasty knee<br>8. Anesthesia – upper leg (except knee)<br>9. Medical examination/evaluation<br>10. Implant, device or graft related encounter - hip | 1. Professional Fees<br>2. E and M – Prolonged services<br>3. Other vascular catheterization; non heart<br>4. Traumatic brain injury (TBI); concussion, initial encounter<br>5. Trauma Response<br>6. Respiratory failure; insufficiency; arrest<br>7. Acute pulmonary embolism<br>8. PERCUTANEOUS CARDIOVASCULAR PROCEDURES WITH DRUG-ELUTING STENT WITHOUT MCC<br>9. Diagnostic cardiac catheterization; coronary arteriography<br>10. E and M – Transitional care management services<br>11. *Acute myocaridal infarction* | 1. Gastrectomy; partial and total<br>2. O.R. PROCEDURES FOR OBESITY WITHOUT CC/MCC<br>3. Other OR upper GI therapeutic procedures<br>4. Incision, Excision, Laparoscopic and Introduction Procedures on the Stomach<br>5. Medical Services – medical nutrition therapy<br>6. Obesity<br>7. Post-procedural and postoperative digestive system complication<br>8. Gastritis and duodenitis<br>9. Surgery – endocrine system<br>10. Gastroduodenal ulcer | 1. Diagnostic cardiac catheterization; coronary arteriography<br>2. Percutaneous transluminal coronary angioplasty (PTCA) with or without stent placement<br>3. PERCUTANEOUS CARDIOVASCULAR PROCEDURES WITH DRUG-ELUTING STENT WITHOUT MCC<br>4. Heart failure<br>5. E and M – Transitional care management services<br>6. Nonrheumatic and unspecified valve disorders<br>7. Coronary Care<br>8. Other and ill-defined heart disease<br>9. Myocarditis and cardiomyopathy<br>10. Cardiac dysrhythmias |

*FIG. 4*

MACHINE LEARNING AUGMENTED SYSTEM FOR MEDICAL EPISODE IDENTIFICATION AND REPORTING

BACKGROUND

The present application relates generally to an improved data processing apparatus and method and more specifically to machine learning automated mechanism for medical episode identification and reporting.

Information technology trends in the practice of medicine have made a push to integrate medical records of various computing systems, such as in consolidated patient electronic medical record (EMR) repositories. As such, medical personnel have access to larger sets of medical data for their patients. However, this leads to problems in that the medical personnel must sift through the large amounts of available data to find the data that is of interest to them and their current purpose for accessing the data, i.e., typically for the purpose of treating the patient. It is not practical for a human being to be able to generate all the correlations between individual portions of data, across potentially multiple different computer-based reporting systems, over various periods of time, and determine what data corresponds to the same meaningful set of events and conditions of the patient.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions executed by the processor to configure the processor to implement a medical episode analysis engine. The method comprises generating a first matrix data structure, comprising a temporally weighted concept relatedness matrix, based on temporal characteristics of concept instances in a plurality of concept instances extracted from input data. The first matrix data structure comprises an entry for each pair of concepts identified in the plurality of concept instances. The entry stores a value representing a base level of relatedness of the corresponding concepts in the corresponding pair of concepts, weighted according to a temporal weighting function and temporal characteristics of the concept instances of the corresponding concepts. The method further comprises generating, by processing the first matrix data structure, a second matrix data structure, comprising a temporally weighted co-occurrence frequency correlated relatedness matrix. The second matrix data structure comprises, for each entry in the first matrix data structure, a measure of a relatedness of the corresponding concepts in the pair of concepts based on a frequency of occurrence, of the concepts in the pair of concepts, occurring together in the input data.

The method also comprises generating, for each first concept in the plurality of concept instances, a concept embedding data structure based on the second matrix data structure. The concept embedding data structure specifies, for each other second concept, a measure of temporally weighted relatedness of the first concept with the second concept. Moreover, the method comprises generating, for each of one or more anchor concepts, a corresponding episode definition data structure comprising a plurality of related concepts corresponding to a same episode, based on the concept embedding data structures, to thereby generate one or more episode definition data structures. In addition, the method comprises processing new input data based on the one or more episode definition data structures to identify instances of corresponding one or more episodes in the new input data.

In other illustrative embodiments, a computer program product comprising a computer useable or readable medium having a computer readable program is provided. The computer readable program, when executed on a data processing system, causes the data processing system to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 4 is an example diagram illustrating a selection of a top-N number of medical concepts occurring in medical episodes of patients for generation of general medical episode definitions in accordance with one illustrative embodiment;

DETAILED DESCRIPTION

Figure 1A:
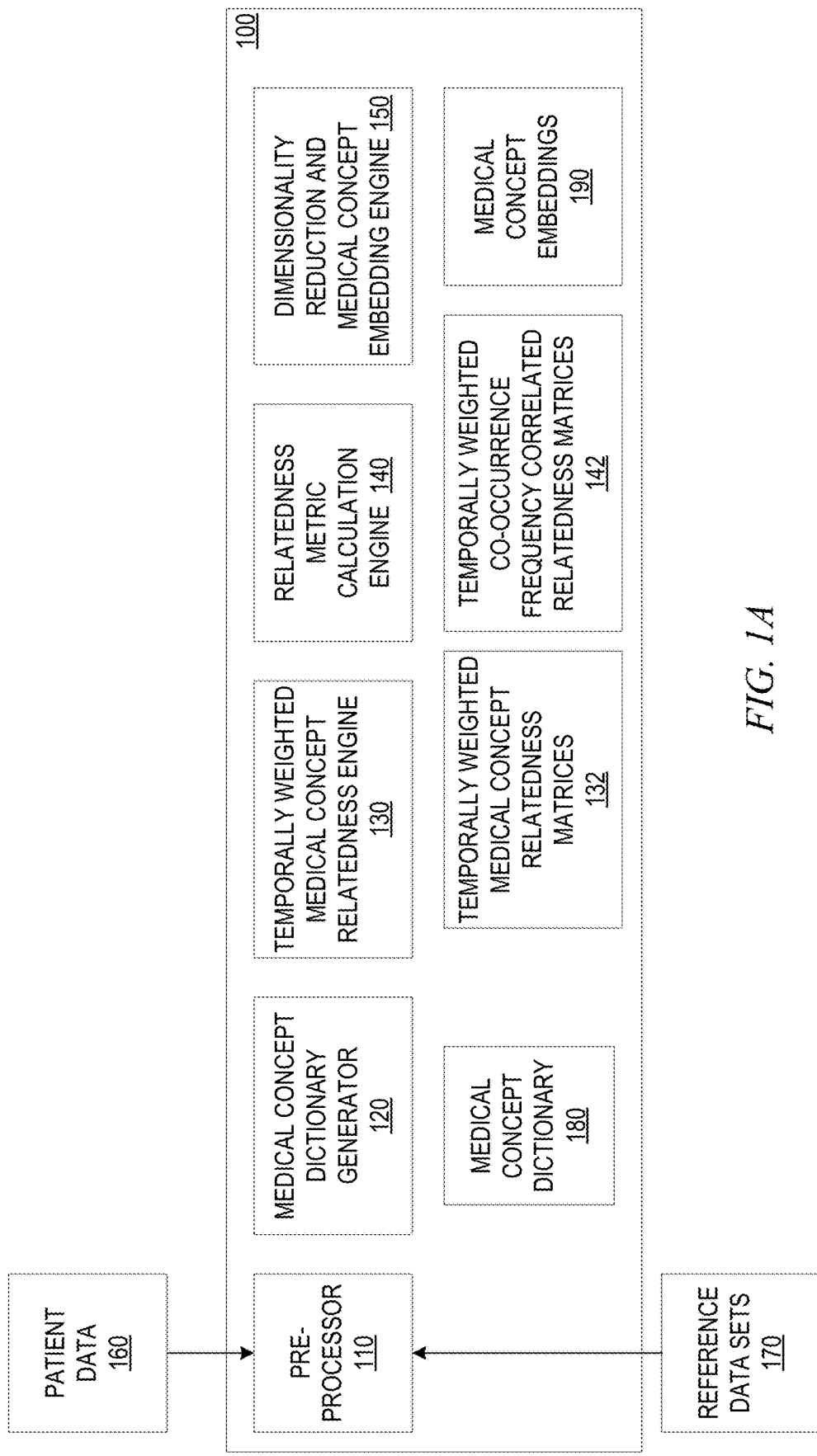
FIG. 1A is an example block diagram illustrating the primary elements of a medical concept embedding generation computer pipeline in accordance with one illustrative embodiment.

As mentioned above, recent trends in medical information technology involve integrating computing systems from various sources, e.g., hospitals, clinics, doctor offices, medical insurance companies, pharmacies, medical laboratories, etc., such that a comprehensive patient electronic medical record (EMR) is generated for patients compiling all of their medical information from the various source computing systems. As such, a large amount of data is available to medical personnel to assist with evaluating the medical conditions, medical history, and the like, of the patient, all with an aim at improving the way in which the patient receives treatments for their medical condition. Of course, other uses for such consolidated patient EMR data may be made as well by various users depending on the desired implementations, e.g., statistical analysis, outbreak detection, medical insurance payment evaluations, etc.

Problems exist when such large amounts of data are compiled in that the volume of data often makes it difficult to pinpoint or identify the particular information about a patient that a medical professional, or other individual or organization-based user, is most interested in. For example, a typical patient's record over a period of 10 or more years could easily have 100,000 elements of information ranging from problem lists, recorded diagnosis, visit summaries, medications, labs, medical insurance claims, etc. Furthermore, these records may comprise various medical codes of various medical coding standards as such medical coding standards change over time, patients move from one medical insurance coverage to another, receive medical services from various service providers in various geographical areas, etc. In short, there is a large amount of variability in the compiled data which makes it difficult, and practically impossible, for a human being to be able to draw correlations, especially when one is looking at more than one patient, such as in the case of evaluating patient data for epidemiological analysis, evaluating patient data for medical billing and cost projection, evaluation of bundled payment programs, performing hospital or medical facility administrative tasks, or the like.

Even on the single patient level of care, it is often difficult for a medical practitioner to be able to correlate data in the volumes of medical history information for a single patient, especially when such data is compiled from various source computing systems. One solution to this problem, both for a single patient and across multiple patients, is to organize the patient data for a patient into medical episodes that the patient has experienced. A medical episode is a set of medical encounters with the patient, medical diagnoses, treatments, and the like, that are related to one another and may be associated with a same set of one or more medical conditions for which the patient has sought medical assistance.

However, even if one were to attempt to manually identify medical episodes, such manual effort would require knowledge spanning multiple different medical specialties, and will be an extremely time intensive process. Moreover, even if one were to try to identify medical episodes, one would need to use fixed time windows just to try to limit the data evaluated, which would result in the potential loss of information and inaccurate results, especially when one realizes that the same time window is not applicable to all types of medical episodes or complexity of patient medical conditions. Thus, even if one were to attempt to manually identify medical episodes in a patient's medical history data records, such manual efforts are rife with errors since it is highly likely that all related elements of the patient records are not easily found through manual examination and non-related elements are highly likely to be mistakenly included in a medical episode due to the inherent limitations of human mental and physical capabilities.

Moreover, the grouping of healthcare information for patients into clinically meaningful episodes is an essential analytic tool for comparing cost and quality of care across patients, providers, and health plans. For example, government healthcare programs, such as Medicare, and commercial health plans are increasingly transitioning to value-based payment models, such as bundled payments, that operate based on medical episode definitions of included and excluded services. Coded criteria for services included and excluded in a medical episode of care are based on clinical knowledge of the condition and its treatment protocols. However, the identification of medical episodes requires multi-specialty, clinical and nosology expertise. Moreover, as touched upon above, such medical episode identification is largely a manual effort but is such a detail intensive and time consuming process that it is impractical to perform for individual patients, let alone scale to any appreciable level beyond individual patients.

The illustrative embodiments provide an improved computer tool for performing automatic detection and reporting of medical episodes in patient medical data, which may be obtained from various source computing systems, such as computing systems associated with different medical facilities, medical practitioners, medical insurance claims processing systems, or any other computing systems storing data regarding patient encounters, patient clinical values, medical insurance claims processing, and/or other patient medical services obtained by the patient in addressing their medical and/or mental health. It should be appreciated that while the illustrative embodiments will be described with reference to medical episodes and medical/clinical data for patients, the illustrative embodiments are not limited to such. To the contrary, the illustrative embodiments may also be implemented with regard to data regarding the mental condition of the patient and services, measured values, and service information directed to the addressing of the mental condition of the patient. In some illustrative embodiments, such episode based evaluations as presented by the mechanisms of the illustrative embodiments may be applied to other areas that are not medical or mental conditions of human beings but rather associated with other biological entities, e.g., veterinary practices associated with animals as the "patients", information technology environments where the computing devices and/or software systems may be considered the "patients", scientific pursuits in which subjects of experimentation may be considered the "patients", etc. In short, the mechanisms of the illustrative embodiments may be applied to any situation where large volumes of data are obtained for particular subjects where subsets of this data may be correlated into episodes, where each episode corresponds to data directed to a same condition and services/events/measured values corresponding to that same condition.

The improved computing tool of the illustrative embodiments implements an unsupervised machine learning computing tool that generates initial groupings of patient electronic medical record (EMR) data, describing clinical values, medical conditions, medical services and procedures obtained/performed, medications prescribed/taken, various medical codes for insurance claims, etc., for patients into medical episodes using real-world data. The improved computing tool of the illustrative embodiments learns semantic relations among the patient EMR data, e.g., the services, procedures, conditions, medications, etc., from the real-world data and finds common patterns by aggregating patient-level relationships over a large sample. These learned semantic relationships and common patterns are used to create groupings of patient EMR data for a large sample of patients.

For a medical condition of interest, for example, groups of patient EMR data may be selected that include this medical condition and medical treatment/services, etc. associated with the groups of patient EMR data may be identified in order to summarize the frequency of occurrence of these medical treatments/services with regard to the medical condition. Based on the frequency of occurrence of these medical treatments/services in relation to the medical condition, medical episodes may be defined, filtering out medical treatments/services and/or other patient EMR data, that are determined to be irrelevant due to low frequency of occurrence, e.g., below a predetermined threshold of occurrence, and adding in medical treatments/services and/or other patient EMR data of relevance due to frequencies of occurrence being equal to or above a threshold frequency of occurrence.

By providing an improved computing tool implementing unsupervised machine learning mechanisms to learn semantic relationships among medical concepts, such as medical services, procedures, medical conditions, medications, clinical values, etc., from real-world data, the mechanisms of the illustrative embodiments eliminates the need for varied expertise across multiple medical specialties. That is, as long as the medical specialty is represented in the patient EMR data used to train the unsupervised machine learning mechanisms for identifying medical episodes, then the medical specialty knowledge will be represented in the trained machine learning mechanisms. Moreover, the improved computing tool mechanisms of the illustrative embodiments save time and manual effort required to produce new medical episode definitions from scratch. Furthermore, the improved computing tool mechanisms significantly reduce errors introduced into medical episode definitions due to human limitations. In addition, improved computing tool mechanisms allow for variable size time windows when it comes to identifying medical episodes, such that a same fixed time window is not applied to all medical episode definitions, but rather different types of medical episodes may have differing time windows for identifying data that is part of the same medical episode.

It should be appreciated that once medical episodes are defined through the application of the unsupervised machine learning based computing tools of the illustrative embodiments, the illustrative embodiments may evaluate patient EMR data to identify medical episodes for patients, or across patients, and present medical episode summaries for individual patients as well as aggregated medical episode summary information across patients. These medical episode summaries may be presented in different manners for different users based on the intent of the usage of the medical episode summaries. For example, medical episode summaries for individual patients may be presented to users, such as medical professionals, for evaluating individual patient medical conditions and determine appropriate care paths. Moreover, medical episodes summaries across multiple patients may be presented to medical professionals, to identify the medical treatments, services, etc., that are most typically associated with a given anchor procedure. For example, if a patient were to undergo a knee replacement procedure, the mechanisms of the illustrative embodiments, by automatically learning the relationships between medical concepts associated with knee replacement from real-world data of actual patients who underwent knee replacements, can determine the typical collection of treatments, services, therapies, etc., including pre- and post-operative ones that are most likely to be one this patient will encounter as part of the episode, and present that information to the medical professional, patient, or other user. This medical episode information may be used in various ways for planning purposes, cost evaluation, predicting likelihood of success of treating the medical condition and/or risks involved, etc. In other illustrative embodiments, the medical episode information across a plurality of patients may be used for epidemiological analysis and prediction.

These summaries may be organized and presented to a user, such as a medical professional, medical insurance representative, medical laboratory technician, medical specialist, the patient, or the like, for assisting the user in understanding the medical condition of the patient in a concise and easy to access manner that does not require that the user sift through voluminous amounts of patient EMR data and make mental notes and correlations amongst the large amount of data. The particular summaries may be generated based on a specification of the types of medical episodes that the user wishes to be informed of. For example, the user may specify one or more characteristics of a type of medical episode that the user is interested in viewing summary information about, e.g., particular medical condition or medical concept of interest, such as specific diseases, medications, encounters, etc., severity of episodes, and the like. Such an input from the user can be taken at set up time or each time a patient summary is desired through a user interface in which the user, e.g., a clinician, requests the type of information sought. Since the information recorded in the EMRs for the patients may not be described in the same way as the request, a concept name mapping algorithm may be employed to translate such a request to a known vocabulary.

The summary may be output to the user in a graphical user interface with a drill down capability. That is, the user may select medical issue summaries or medical episode summaries and drill down into the particular sub-elements that contribute to the summary, e.g., the particular medical episodes that comprise the medical issue summary, the particular medical concepts associated with the selected medical episode, or the like. Thus, the user may be presented a graphical user interface with the summaries corresponding to the user's specified interest, and may then select the summaries within the graphical user interface where the user wishes to see more detailed information about the medical episode.

Hence, the mechanisms of the illustrative embodiments provide an improved computerized tool for analyzing voluminous patient medical information, such as in a consolidated patient electronic medical record (EMR) where data from a variety of different medical computing systems are compiled, and automatically learning, through unsupervised machine learning mechanisms, the relatedness of medical concepts with regard to defining medical episodes, taking into account temporally weighted concept relationships. The mechanisms of the illustrative embodiments provide a medical concept embedding mechanism based on an automatically generated concept dictionary, temporally weighted concept relatedness analysis, and dimensionality reduction operation. The "embeddings" are a mapping of discrete variables, e.g., medical concepts, to a vector of continuous values. In the context of the illustrative embodiments and the machine learning mechanisms described herein, these embeddings are a learned translation of medical concepts into continuous vector representations in a multi-dimensional vector space. The illustrative embodiments utilize the automatically learned concept embeddings to vectorize patient EMR data and compute pair-wise vector similarity and pairwise temporal weightings, allowing for clustering of the vectorized patient EMR information. The clustered information may then be used to generate medical episode definitions.

Through defining medical episodes in this manner from the real-world data, potentially across multiple medical disciplines, medical episode definitions may be automatically generated and portions of patient EMR data corresponding to medical episodes may be identified based on the medical episode definitions. This medical episode information may be stored in association with the patient medical information or patient EMR data for use in outputting graphical user interfaces (GUIs) comprising summaries of medical episodes for users. The particular summaries presented in the GUIs may be based on user specified criteria. Moreover, the summaries are selectable and able to be drilled down to obtain the details of the particular summary, e.g., medical concepts, etc. These mechanisms alleviate the burden on users to sift through large amounts of medical data to identify medical data relevant to the particular purpose for which the user wishes to access the patient medical information.

Before continuing the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for automatically learning relationships between medical concepts from real-world patient EMR data and generating medical concept embeddings based on these learned relationships. Moreover, the present invention provides mechanisms for defining medical episodes based on these learned medical concept embeddings and real-world patient EMR data. For example, in some illustrative embodiments, the learned medical concept embeddings may be applied to patient medical insurance claims information to generate vectors of claims information that may then be used to perform pairwise similarity analysis, clustering, and generation of medical episode definitions based on the results of such similarity analysis and clustering.

As mentioned above, there are two primary components to generating medical episode definitions through an automatic unsupervised machine learning process using unsupervised machine learning computer models, such as neural network computer models. A first primary component is a medical concept embedding component that learns relationships between medical concepts and generates medical concept embeddings based on these automatically learned relationships. A second primary component is an unsupervised grouping component that groups medical concepts into medical episodes using the learned medical concept embeddings. These primary components will now be described in greater detail with reference to FIGS. 1A-1B and 2A-2B.

FIG. 1A is an example block diagram illustrating the primary elements of a medical concept embedding generation computer pipeline in accordance with one illustrative embodiment. It should be appreciated that, in some illustrative embodiments, the elements of FIG. 1A may be implemented as software instructions executed on computer hardware of one or more computing devices to thereby specifically configure those one or more computing devices to be special purpose computing devices that operate to perform the specific non-generic computer operations described hereafter as attributed to the elements that they are configured to implement. It should also be appreciated that, in some illustrative embodiments, the elements of FIG. 1A may be implemented as dedicated computer hardware devices that are specifically configured in the hardware itself, e.g., through wiring, circuitry, configuration of logic gates, firmware, etc. to operate as one or more of the elements shown in FIG. 1A and perform the non-generic computer operations described hereafter as attributed to the elements that they are configured to implement. Moreover, in other illustrative embodiments, a combination of software executed on computer hardware and dedicated computer hardware elements may be used without departing from the spirit and scope of the present invention. Regardless of the particular software/hardware configuration chosen for the particular implementation of the illustrative embodiments, it should be appreciated that the illustrative embodiments are directed to an improved computer tool and improved computer tool operations for automated machine learning of medical concept embeddings and generation of medical episode definitions that are then applied to patient EMR data to generate identified medical episode information for a variety of different uses.

As shown in FIG. 1A, the medical concept embedding generation computer pipeline 100 (hereafter referred to as the "embedding pipeline") includes a pre-processor 110, a medical concept dictionary generator 120, a temporally-weighted medical concept relatedness engine 130, and a relatedness metric calculation engine 140, and a dimensionality reduction and medical concept embedding engine 150. As shown in FIG. 1A, these elements 110-150 operate in conjunction with and/or generate various data structures including real-world patient data 160, reference data sets 170, medical concept dictionary 180, and medical concept embeddings 190. It should be appreciated that while these elements 110-190 are explicitly shown in FIG. 1A, there may be other elements, such as communication interfaces, network adapters, storage devices, memories, controllers, and the like, that provide underlying functionality and resources to facilitate the non-generic computer operations of the depicted elements 110-150.

The operation of these primary elements 110-150 in conjunction with the data structures 160-190 will be described with regard to medical concepts corresponding to medical codes according to one or more medical coding standards, however, the illustrative embodiments are not limited to such. Rather, the medical concepts may be represented in input real-world patient data 160 in various manners including medical codes which may appear in content or metadata of the patient data 160, but also in natural language content provided in free-form text or structured elements of patient data records, for example. In the case of natural language content in the real-world patient data 160, computerized natural language processing mechanisms may be executed on the natural language content of the real-world patient data 160 to extract terms/phrases indicative of medical concepts, such as based on medical knowledge resources, e.g., reference data sets 170. The medical knowledge resources, e.g., reference data sets 170, may comprise dictionary data structures for medical terminology, pharmaceutical reference texts and/or medication information resource data structures generated by pharmaceutical providers or medical organizations, medical journals, medical research documents, and the like, which may be processed during an ingestion process to extract medical concepts and corresponding terms/phrases, etc. Moreover, medical coding scheme documentation, laboratory notation resource documentation, and the like, may also be used as part of the knowledge resources, e.g., reference data sets 170, to identify elements of real-world patient data 160 that are indicative of particular recognizable medical concepts.

Any source of medical knowledge that may be represented in a data structure which can then be used to correlate with instances of the alphanumeric strings in real-world patient data 160 may be used as part of the natural language processing of the patient data 160 without departing from the spirit and scope of the illustrative embodiments. For example, processing the compiled real-world patient data 160 may result in instances of medical concepts corresponding to medical conditions, e.g., diseases, treatments, medical services, laboratory results, medications, and the like, being extracted from the real-world patient data 160 based on the correlation of text/clinical values/medical codes in the real-world patient data 160 with instances in the knowledge resources, e.g., reference data sets 170, utilized to extract the instances of medical concepts.

Thus, the pre-processor 110 comprises logic for pre-processing the input real-world patient data 160 and extracting recognizable medical concepts from the real-world patient data 160. It should be appreciated that the real-world patient data 160 may be obtained from a variety of different source computing systems and/or data storage systems, such as via one or more data networks. The real-world patient data 160 may be compiled, for example, through a medical data warehouse system that compiles patient data from various source computing systems including medical practice computing systems, hospital computing systems, pharmacy computing systems, clinic computing systems, medical insurance organization computing systems, and the like. Essentially, any computing systems that are able to collect, store, and report patient data may be a source of patient data for purposes of providing real-world patient data 160. The data may represent inpatient and outpatient services, treatments, medications, prescriptions, procedures, diagnoses, clinical values, medical claims, etc.

The medical concept dictionary generator 120 comprises logic that operates to take the extracted medical concepts and "roll-up" extracted medical concepts into higher-level logical categories of medical concepts in order to address potential extracted instances of different medical concepts referencing similar overall medical concepts. For example, using medical codes as the extracted medical concepts extracted from the real-world patient data 160, many different medical codes may all reference a similar overall medical concept, e.g., many different medical codes may all mean "heart failure" or "diabetes", and in order to make machine learning of relationships between medical concepts more accurate and meaningful it is beneficial to correlate these disparate medical codes to a common overall medical concept. Thus, the medical concept dictionary generator 120 comprises logic to correlate extracted instances of medical concepts extracted through the pre-processing with overall medical concepts that are at a higher level in an ontology of medical concepts through a mapping, via an ontology data structure, of lower level medical concepts with higher level categories of medical concepts that encompass multiple different lower level medical concepts.

The temporally weighted medical concept relatedness engine 130 comprises logic that operates to generate one or more temporally-weighted medical concept relatedness matrices 132 that represent the relative level of relatedness of medical concepts based on the temporal relationships. That is, the logic of the temporally weighted medical concept relatedness engine 130 operate to perform pattern analysis on the extracted medical concept instances in the pre-processed patient data and determine a measure of relatedness based on a frequency of occurrence of medical concepts with each other, but additionally weighted based on the closeness of time between the co-occurring medical concepts. That is, medical concepts that co-occur in patient data are given a base level of relatedness based on a frequency of co-occurrence in the patient data. Moreover, the level of relatedness is further weighted based on how close in time the co-occurring medical concepts are to each other, with relatively temporally closer co-occurring medical concepts being given higher weights, and thus measures of relatedness, than co-occurring medical concepts that are relatively more distant temporally from each other. The resulting one or more temporally-weighted medical concept relatedness matrices 132 comprises entries corresponding to medical concepts with measures specifying the temporally weighted relatedness of pairs of medical concepts, e.g., for each pair of medical concepts in the generated medical concept dictionary, a corresponding slot in the matrix comprises a temporally weighted measure of relatedness of the two medical concepts.

The relatedness metric calculation engine 140 operates on the one or more temporally weighted concept relatedness matrices 132 to evaluate whether concepts co-occur more frequently within a given context than if these co-occurring concepts were independent. The relatedness metric calculation engine 140 generates, for each pair of medical concepts in the one or more temporally weighted concept relatedness matrices, weighted according to temporal factors as noted above, a measure of correlation, or relatedness, between the two medical concepts, where this measure may be proportional to the number of times both medical concepts occur together and is inversely proportional to the individual counts of the medical concept occurrences separately. For example, a positive point-wise mutual information (PPMI) based evaluation may be performed by the logic of the relatedness metric calculation engine 140. Thus, for each pair of medical concepts present in the one or more temporally weighted concept relatedness matrices 132, a corresponding measure of correlation, or relatedness, between the two medical concepts is also stored in the entry of the one or more temporally weighted concept relatedness matrices 132 corresponding to the intersection of these two medical concepts, thereby generating one or more temporally weighted and co-occurrence frequency correlated relatedness matrices 142.

The dimensionality reduction and medical concept embedding engine 150 operates on the one or more temporally weighted and co-occurrence frequency correlated relatedness matrices 142 to reduce the dimensionality of the matrices. The dimensionality reduction and medical concept embedding engine 150 generates a lower dimensional, dense vector representation of the one or more temporally weighted and co-occurrence frequency correlated relatedness matrices 142 and thereby generates a medical concept-to-vector dictionary or embedding matrix data structure 190 that is then able to be used to vectorize other patient data for purposes of generating medical episode definitions, as discussed hereafter with regard to FIGS. 2A and 2B.

Figure 1B:
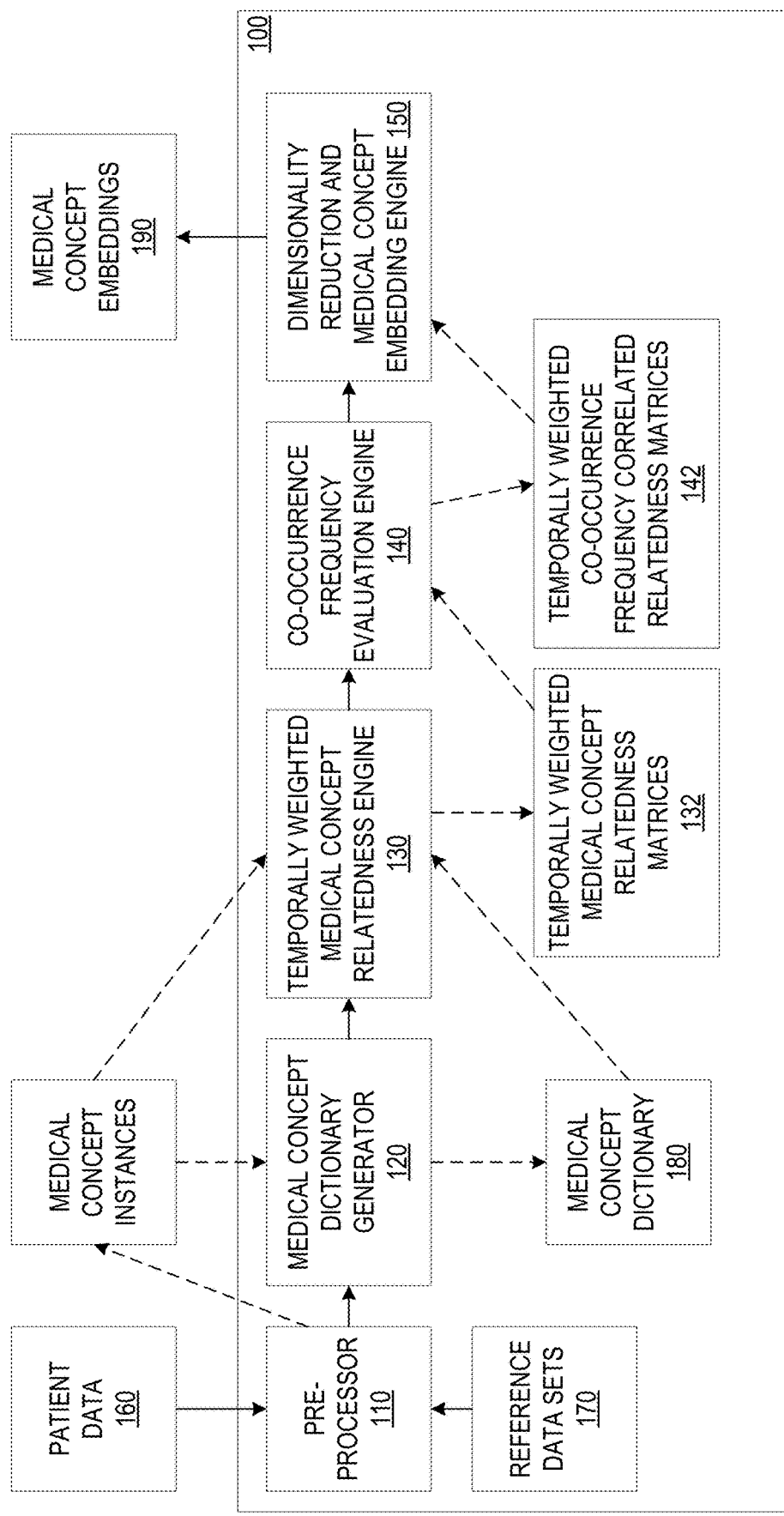
FIG. 1B is an example block diagram illustrating an operational flow of the embedding pipeline of FIG. 1A in accordance with one illustrative embodiment.

FIG. 1B is an example block diagram illustrating an operational flow of the embedding pipeline 100 of FIG. 1A in accordance with one illustrative embodiment. In the depicted example, it will be assumed that the input patient data 160 comprises medical insurance claims data for inpatient and outpatient services, prescriptions, procedures, and other medical insurance claims data for a plurality of patients. In such a depicted example, the mechanisms of the illustrative embodiments may be implemented to perform medical episode identification and identification of the services, prescriptions, procedures, etc. associated with medical episodes, such as for purposes of treatment cost predictions, bundled payment estimations, patient advising, and/or the like, for example. Thus, in the depicted example, the patient data 160, such as medical claims data is processed to identify medical code instances in the patient data and then learn relationships between the medical concepts corresponding to the medical code instances so as to generate medical concept embeddings which are then used to define medical episodes.

As shown in FIG. 1B, the patient data 160 is collected and input to the pre-processor 110 which normalizes and maps the medical codes to medical concepts using reference data sets 170, such as medical coding standards data structures, medical concept ontologies, and the like. For example, the reference data sets 170 may specify medical codes and their corresponding medical concepts or definitions and this standard of medical codes may be used to identify instances of the medical codes present in structured and/or unstructured content of the patient data 160. The pre-processor 110 extracts the instances of medical codes found through a parsing and processing of the input patient data 160, and in some illustrative embodiments by applying computerized natural language processing on natural language content of the input patient data 160, and provides these extracted instances of medical codes to the medical concept dictionary generator 120 and temporally weighted medical concept relatedness engine 130 for further processing as part of the pipeline 100.

Thus, for example, the pre-processor 110 may parse and analyze the input patient data 160 and identify ICD-10 PCS codes, CPT codes, UB-04 revenue codes, ICD-10 CM Diagnosis codes, and/or the like, and the medical concept dictionary generator 120 generates the medical concept dictionary 180, which may include correlating the identified medical code instances, where possible, with category or group level codes based on a mapping of the medical codes to such categories or groups as specified in the reference data sets 170, e.g., 10 different medical codes, such as a first code for type-1 diabetes, a second code for type-2 diabetes, gestational diabetes, prediabetes, etc., that all reference a similar medical condition may be mapped to the same medical condition category code, e.g., "diabetes". Thus, instances of medical codes found in the patient data 160 may be "rolled-up" into higher level group or category level codes. Each of the individual medical codes, as well as the higher level group or category level codes, may have corresponding descriptions defining what those medical codes or group/category level codes represent, with these descriptions also being provided in the reference data sets 170. Thus, the resulting medical concept dictionary 180, in an example illustrative embodiment based on identification of medical codes, may comprise a structured data structure of individually recognized medical codes, their mappings to group/category codes, and corresponding descriptions.

The temporally weighted medical concept relatedness engine 130 receives the medical concept dictionary 180 and the identified instances of medical concepts, e.g., medical codes, from the pre-processor 110 as input. The identified instances of medical concepts received from the pre-processor 110 may be provided in the form of matrices, each matrix being associated with a corresponding patient in a plurality of patients, where the matrix is organized to pair identified medical concepts, e.g., medical codes, in the patient data 160 corresponding to the patient, or such matrices may be generated by the temporally weighted medical concept relatedness engine 130 from the received identification of instances of medical concepts (medical codes) from the pre-processor 110. For each pairing of medical codes (which are considered in this example to be the medical concepts), the temporally weighted medical concept relatedness engine 130 determines a temporal weighting indicating a temporal correlation between the medical codes in the pairing and stores that temporal weighting in association with the pairing, e.g., in the cell of the matrix data structure corresponding to the intersection of the two medical codes.

The temporally weighted medical concept relatedness engine 130 operates based on the recognition that counts of the number of co-occurrences of the medical concepts in the patient data 160 is not sufficient to determine relatedness for purposes of medical episode identification. That is, in other disciplines, such as natural language processing (NLP), term-term co-occurrence is derived by counting how often a first term appears along with a second term within a document or a sentence. However, in the patient data case, the patient represents a top-level context and given the heterogeneity of medical concepts, such as medical conditions, procedures, treatments, etc., that a particular patient may have, simply capturing concept co-occurrence at a patient level is not a good measure of relatedness between these medical concepts. For example, consider a patient with a chronic medical condition of diabetes who undergoes a knee replacement procedure. In such a case, an office visit for diabetes management is unlikely to be directly clinically related to the knee replacement procedure.

From the perspective of episodes of care, or medical episodes, it is recognized that events close in time tend to be more closely related than those that are temporally further apart. To quantify this, the temporally weighted medical concept relatedness engine 130 implements a concept-to-concept (code-to-code) relatedness measure that is exponentially attenuated by their temporal separation. This temporal weighting of the concept-to-concept relatedness measure provides a semantic encoding of the medical concepts, or medical codes.

Concretely, for every pair of medical concepts (e.g., medical codes) within a patient's patient data, e.g., medical insurance claims data and/or other patient electronic medical record (EMR) data, a maximal time-scaled relatedness value is captured in a temporally weighted medical concept relatedness matrix 132, i.e., a matrix $R_m \in \mathbb{R}^{C*C}$, where C is the size of the medical concept dictionary, or vocabulary V, $\{c_i: i | 1 \leq i \leq V\}$. An exponential time-scaling function is used, e.g., $$\exp\left(\frac{-|\Delta t_{i,j}|}{T_c}\right),$$

where $\Delta t_{i,j}$ is the gap in time between occurrences of the medical concepts i and j, e.g., medical codes i and j. That is, for example, in the case of medical insurance claims, $\Delta t_{i,j}$ is the gap in time between service dates of the medical insurance claims from which the medical concepts i and j originated. $T_c$ is a parameter to control the rate of decay. The individual patient matrices generated by evaluating these pairings in the patient data for the patients may be combined to produce an overall temporally weighted relatedness matrix R, across all patients (or members M) sampled from the patient data 160, $R = \Sigma_{m=1}^{M} R_m$.

Thus, the exponential function as described above provides a real number with the relatedness being based on time gap and co-occurrence being indirectly captured. In some cases, where there are multiple co-occurrences of the same two medical concepts, a maximum of the exponential function value for a given medical concept may be utilized, e.g., use the least time gap since it will have a negative exponential and calculate the corresponding exponential function value. Across medical concepts, or elements, the above function is calculated for each medical concept or element depending on their time gap and then all of those values are summed. Thus, other medical concepts or elements may have a different least time gap and the exponential function will be calculated accordingly.

The relatedness metric calculation engine 140 operates on the one or more temporally weighted concept relatedness matrices 132 to evaluate whether concepts co-occur more frequently within a given context than if these co-occurring concepts were independent. The relatedness metric calculation engine 140 generates, for each pair of medical concepts in the one or more temporally weighted concept relatedness matrices, weighted according to temporal factors as noted above, a measure of correlation between the two medical concepts, where this measure may be proportional to the number of times both medical concepts occur together and is inversely proportional to the individual counts of the medical concept occurrences separately. For example, a positive point-wise mutual information (PPMI) based evaluation may be performed by the logic of the relatedness metric calculation evaluation engine 140. Thus, for each pair of medical concepts present in the one or more temporally weighted concept relatedness matrices 132, a corresponding measure of correlation between the two medical concepts is also stored in the entry of the one or more temporally weighted concept relatedness matrices 132 corresponding to the intersection of these two medical concepts, thereby generating one or more temporally weighted and co-occurrence frequency correlated relatedness matrices 142.

For example, the relatedness metric calculation engine 140 may take the combined overall temporally weighted relatedness matrix R in the one or more temporally weighted medical concept relatedness matrices 132 and apply a PPMI analysis to the temporally weighted co-occurrence values in the matrix R. For example, the PPMI analysis may calculate a PPMI measure using the following relationship:

$$pmi(c_i, c_j) = \log_2\left(\frac{p(c_i, c_j)}{p(c_i)p(c_j)}\right),$$

$$\text{where } p(c_i, c_j) = \frac{r_{i,j}}{\Sigma_{i=1}^{N}\Sigma_{j=1}^{N} r_{i,j}}, \ p(c_i) = \frac{\Sigma_{j=1}^{N} r_{i,j}}{\Sigma_{i=1}^{N}\Sigma_{j=1}^{N} r_{i,j}},$$

$$p(c_j) = \frac{\Sigma_{i=1}^{N} r_{i,j}}{\Sigma_{i=1}^{N}\Sigma_{j=1}^{N} r_{i,j}}, \text{ and } ppmi(c_i, c_j) = \max(pmi(c_i, c_j), 0)$$

where $r_{i,j}$ is the entry in the i'th row and j'th column in the relatedness matrix R.

Thus, the relatedness metric calculation engine 140 generates one or more temporally weighted and co-occurrence frequency correlated relatedness matrices 142. These one or more matrices 142 are input to the dimensionality and medical concept embedding engine 150 which operates on them to reduce the dimensionality of the one or more matrices 142. The dimensionality reduction and medical concept embedding engine 150 generates a lower dimensional, dense vector representation of the one or more temporally weighted and co-occurrence frequency correlated relatedness matrices 142 and thereby generates a medical concept-to-vector dictionary or embedding matrix data structure 190 that is then able to be used to vectorize other patient data for purposes of generating medical episode definitions. For example, the dimensionality reduction and medical concept embedding engine 150 may operate on the one or more matrices 142 by applying, for example, a singular value decomposition (SVD) or other dimensionality reduction algorithm, may be applied to the one or more matrices 142. In an embodiment where SVD is utilized, SVD obtains a lower dimensional, dense vector representation of the one or more matrices 142 where the dense SVD embeddings tend to provide better performance than the relatively sparser matrices 142 with regard to medical concept similarity analysis. Based on the dimensionality reduction, a concept-to-vector dictionary or embedding matrix, $E \in \mathbb{R}^{C*D}: D \leq C$ is generated as a rank-D SVD of the corresponding matrix 142.

Thus, through the process describe above with regard to FIGS. 1A and 1B, the pipeline 100 is able to automatically learn, through a machine learning process, medical concept embeddings based on temporal weighted co-occurrence of medical concepts. These medical concept embeddings may then be used to vectorize patient data and generate definitions for medical episodes as described hereafter with regard to FIGS. 2A and 2B. The machine learning performed by the present invention involves the clustering and relatedness metric evaluation mechanisms described above, which provide optimization of the patient data and learning of medical episodes definitions that may then be applied to other patient data to identify medical episodes and perform other operations, such as predictions and recommendations, based on the medical episode definitions.

Figure 2A:
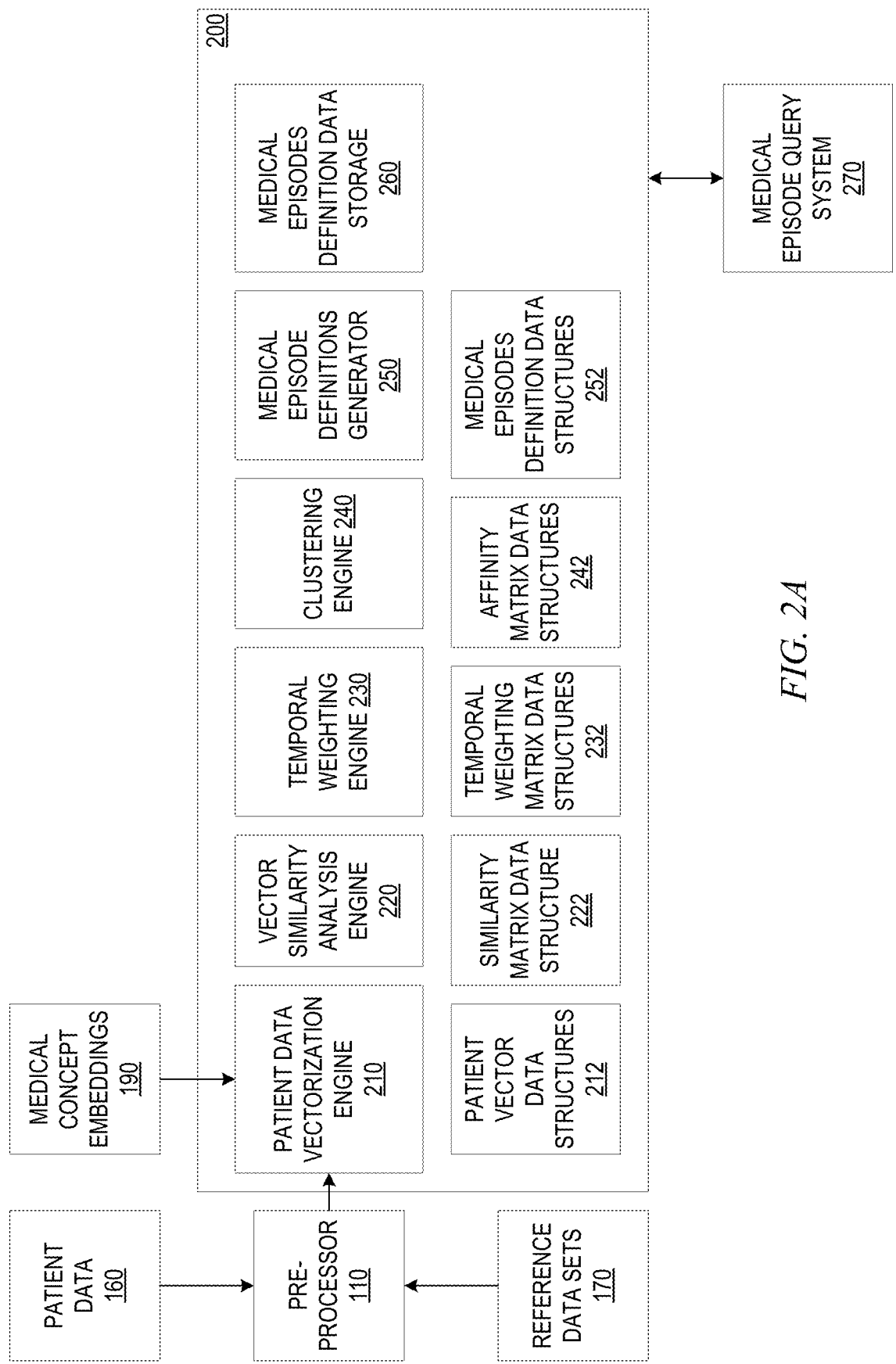
FIG. 2A is an example block diagram illustrating the primary elements of a medical episode definition generation computer pipeline in accordance with one illustrative embodiment.

FIG. 2A is an example block diagram illustrating the primary elements of a medical episode definition generation computer pipeline in accordance with one illustrative embodiment. It should be appreciated that, in some illustrative embodiments, the elements of FIG. 2A may be implemented as software instructions executed on computer hardware of one or more computing devices to thereby specifically configure those one or more computing devices to be special purpose computing devices that operate to perform the specific non-generic computer operations described hereafter as attributed to the elements that they are configured to implement. It should also be appreciated that, in some illustrative embodiments, the elements of FIG. 2A may be implemented as dedicated computer hardware devices that are specifically configured in the hardware itself, e.g., through wiring, circuitry, configuration of logic gates, firmware, etc. to operate as one or more of the elements shown in FIG. 2A and perform the non-generic computer operations described hereafter as attributed to the elements that they are configured to implement. Moreover, in other illustrative embodiments, a combination of software executed on computer hardware and dedicated computer hardware elements may be used without departing from the spirit and scope of the present invention. Regardless of the particular software/hardware configuration chosen for the particular implementation of the illustrative embodiments, it should be appreciated that the illustrative embodiments are directed to an improved computer tool and improved computer tool operations for automated machine learning of medical concept embeddings and generation of medical episode definitions that are then applied to patient EMR data to generate identified medical episode information for a variety of different uses.

As shown in FIG. 2A, the medical episode definition generation computer pipeline 200 (hereafter referred to as the "medical episode pipeline" 200) comprises a patient data vectorization engine 210, a vector similarity analysis engine 220, a temporal weighting engine 230, a clustering engine 240, and a medical episode definitions generator 250 and medical episodes definition data storage 260. As shown in FIG. 2A, these elements 210-250 operate in conjunction with and/or generate various data structures including real-world patient data 160, reference data sets 170, medical concept embeddings data structures 190, patient data vector data structures 212, similarity matrix data structures 222, temporal weighting matrix data structures 232, affinity matrix data structures 242, and medical episodes definition data structures 252. It should be appreciated that while these elements 210-250 are explicitly shown in FIG. 2A, there may be other elements, such as communication interfaces, network adapters, storage devices, memories, controllers, and the like, that provide underlying functionality and resources to facilitate the non-generic computer operations of the depicted elements 210-250.

It should be appreciated that the operation of the medical episode pipeline 200 will be described with regard to processing the patient data for a single patient. However, this process is repeated for each patient represented in the input patient data 160. For example, the input patient data 160 may comprise medical insurance claims data for a plurality of patients, and each patient's data may be separately evaluated through the medical episode pipeline 200 to identify medical episodes associated with that particular patient. These medical episodes for the individual patients may then be collectively evaluated over all of the patients, or a large sample comprising a plurality of patients' medical episode data, to generate medical episode definitions comprising various medical concepts determined to be related to the same anchor medical concept, e.g., medical concepts associated with a particular medical condition, medical procedure, treatment, medication, medical service, or the like.

The patient data vectorization engine 210 comprises logic that operates on the patient data 160, and specifically the medical concepts extracted from the patient data 160 via the pre-processor, to generate a vector representation of that patient data. For example, using medical insurance claims as the patient data, for each claim line in the medical insurance claims data, each line corresponding to a different medical claim, fields of the claim line may be mapped to medical concepts, e.g., medical codes, and each medical code may be embedded using the medical concept embeddings 190 previously automatically determined through the process of FIGS. 1A and 1B above. Thus, the patient data vectorization engine 210 applies the medical concept embeddings to the identified medical concepts and may then sum the embeddings for each medical concept appearing in the claim line to generate a vector representation for the claim line, or claim.

The vector similarity analysis engine 220 comprises logic that operates on the vectorized representations of the patient data to determine a similarity for each of the vector representations of the patient data. That is, claim lines that are more similar to each other are more likely associated with a same medical episode, taking into account again that the medical concept embeddings generated previously take into account temporally weighted co-occurrence of medical concepts in the medical concept embedding. Thus, claim lines having embeddings that are similar according to the similarity evaluation, reference similar medical concepts or highly temporally and co-occurrence related medical concepts, as is reflected in their embeddings. Thus, the embedding transforms each claim line into another vector dimensional space. Similarity is computed across these embeddings in the new vector space and similar claim lines are placed into the same cluster by the clustering mechanisms. Multiple claim lines clustered into the same cluster are part of the same medical episode.

The temporal weighting engine 230 comprises logic that operates, in a similar manner to the temporally weighted medical concept relatedness engine 130, to generate a temporally weighted matrix data structure, but with regard to temporal relatedness of different claim lines in the patient data. Again, there is a basic assumption that claims occurring temporally close to each other are more likely associated with the same medical episode, however this is not necessarily the case. Thus, a combined evaluation of both the vector similarity and the temporal weighting are used to determine whether claim lines are in fact referencing medical concepts associated with the same medical episode. The temporal weighting may use a decay function to again represent the relative likelihood that temporally close claim lines are more likely to be related to one another while temporally distant claim lines are less likely to be related to one another.

The clustering engine 240 comprises logic that operates on the results of the vector similarity analysis performed by the vector similarity analysis engine 220 and the temporal weighting analysis performed by the temporal weighting engine 230 to cluster the medical concepts in the patient data 160 for the patient based on vector similarity and temporal weighting. Thus, medical concepts that appear in claim lines that have relatively higher similarity and higher temporal weight will be clustered together while medical concepts that appear in claim lines that have relatively lower similarity and relatively lower temporal weight will not be clustered together. The strength of the similarity and/or temporal weight will dictate how close or far apart the medical concepts will be in the clustering, such that thresholds may be specified to identify groups or clusters of medical concepts that are considered to be associated with the same medical episode.

The resulting clusters or groupings of medical concepts may be used to generate medical episodes for the patient, e.g., a listing of related medical concepts that corresponding to a medical episode. These medical episodes for each patient may be stored in association with the patient's individual portion of the patient data 160 or otherwise associated with the patient such that the patient has their own associated set of medical episodes that were automatically identified via the medical episode pipeline 200. The medical episodes for each patient may be evaluated in this manner and stored as data structures which may then be analyzed by the medical episode definitions generator 250 to identify medical concepts related to a given anchor medical concept across a plurality of patients and their medical episodes involving that given anchor medical concept.

That is, given an anchor medical concept, such as a medical code for a medical condition or group/category associated with a medical condition, e.g., "diabetes", analysis of medical episodes that patients have which include this anchor medical concept may be identified and the frequency of occurrence of related medical concepts in these defined medical episodes may be evaluated across the various patients. For example, for an anchor medical concept of "diabetes", it may be determined that across 1000 patients, the medical concept of "foot exam" occurs at a frequency of F1, the medical concept of "insulin replacement therapy" occurs at a frequency of F2, the medical concept of "amputation" occurs at a frequency of F3, and the medical concept of "stint" occurs at a frequency of F4. Based on these frequencies of occurrence in medical episodes of patients, it can be determined which medical concepts are most likely to occur, in general, in association with the anchor medical concept in medical episodes. For example, a frequency threshold may be established that specifies a minimum frequency needed to be considered sufficient to include in a general medical episode associated with the anchor medical concept. Thus, if F1 and F2 are equal to or above the threshold frequency TF, then the corresponding medical concepts of foot exam and insulin replacement therapy will be included in the general medical episode definition, and if F3 and F4 are not equal to or above the threshold frequency TF, then they will not be included in the medical episode definition. It should be appreciated that multiple thresholds may be defined for specifying medical concepts that have different probabilities of occurrence, e.g., a first threshold for highly likely medical concepts, a second threshold for relatively likely medical concepts, and a third threshold for unlikely medical concepts.

The resulting medical concepts identified across the various patients may be compiled into a general medical episode definition associated with the anchor medical concept. This can be done for various anchor medical concepts. Thus, for example, a first medical episode definition may be generate for "diabetes" while another medical episode definition may be associated with "heart disease", etc., such that different medical episode definitions may be generated for different anchor medical concepts. Moreover, it should be appreciated that the same medical concept may appear in a plurality of different medical episode definitions, and anchor medical concepts may have a plurality of different medical episode definitions associated with them.

These medical episode definitions may be stored in a medical episode definition storage 260, indexed by anchor medical concept for example, for later use in performing various types of evaluations, such as medical services cost projections, bundled payment analysis for determining a level of bundled payments to be provided for treatment of a particular medical condition, medical services scheduling, etc. For example, by determining the definition of a medical episode in the manner described above, a user may access the medical episode definitions 260 and input a search query for medical episodes associated with a particular medical concept of interest. The corresponding medical episodes may be retrieved and the medical episode definitions may be analyzed using reference data sets 170 to identify costs associated with the medical concepts in the medical episode definition with regard to medical services, treatments, medications, laboratory tests, annual doctor visits, etc., to generate an estimate of the costs to the medical insurance company and to the patient, the compensation provided to the medical professionals and medical facilities, etc.

Figure 2B:
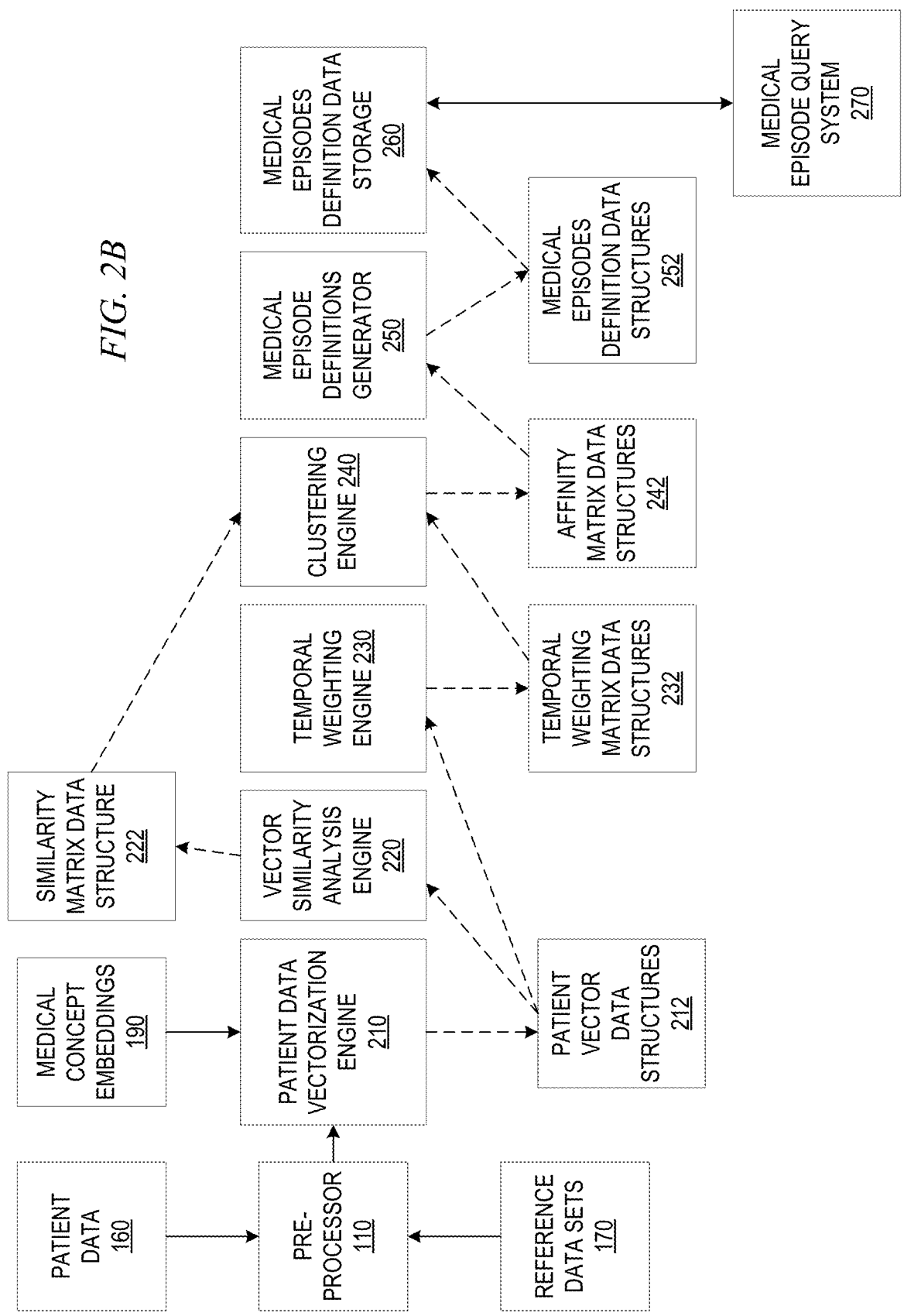
FIG. 2B is an example block diagram illustrating an operational flow of the medical episode pipeline of FIG. 2A in accordance with one illustrative embodiment.

FIG. 2B is an example block diagram illustrating an operational flow of the medical episode pipeline 200 of FIG. 2A in accordance with one illustrative embodiment. As shown in FIG. 2B, the medical episode pipeline 200 operates on patient data, which may be the same patient data 160 as in FIGS. 1A and 1B, or may be a different set of patient data. Similar to the description above, the pre-processor 110 operates on the patient data 160 to parse and extract instances of medical concepts from the patient data 160, such as instances of medical codes present in the patient data 160, e.g., patient medical insurance claims data, using the reference data sets 170 as a basis for this extraction, and in some illustrative embodiments including the use of natural language processing logic to parse and process natural language content of the patient data 160. The resulting instances of medical concepts identified in the patient data 160 are provided as input to the medical episode pipeline 200 along with the previously automatically generated medical concept embeddings 190 generated through the process described with regard to FIGS. 1A and 1B.

The patient data vectorization engine 210 of the medical episode pipeline 200 processes the extracted medical concept instances provided by the pre-processor 110 based on the previously generated medical concept embeddings 190 to generate vector representations 212 for each predetermined portion of patient data, e.g., each claim line in medical insurance claims data for a patient. For example, the patient data 160 may be pre-processed by the pre-processor 110 to identify medical concepts, $c_k$, $1 \leq k \leq C_{CL}$ where $C_{CL}$ is the number of concepts in the portion of patient data, which in this example is a claim line (CL). The vector representation 212 may be generated by combining the embeddings of concepts for the particular portion of patient data, e.g., claim line (CL), i.e., $V_{CL} = \Sigma_{k=0}^{C_{CE}} E(c_k, *)$, where $E(c_k, *)$ represents the vector embedding corresponding to the concept $c_k$ and * represents all entries in that vector. Thus, each portion of patient data will have a corresponding vector representation 212 compiled from the combination of embeddings of medical concepts extracted from that portion of patient data.

After having vectorized all the portions of patient data for the particular patient, e.g., each of the claim lines for claims data for the patient, the vector similarity analysis engine 220 operates on the vectorized representations 212 of the portions of patient data to determine a similarity for each of the vector representations 212 of the patient data. This similarity evaluation may be performed for each pairing of vector representations 212 such that similarity measures are generate for each pair of vector representations 212 across all the vector representations 212 generated for the patient data associated with the patient. In one illustrative embodiment, a cosine similarity matrix S 222 may be generated for each pair of claim line vectors of the patient, where entries in the matrix indicate the cosine similarity of corresponding vector slots in the vector representations 212 for the claim lines. The generation of cosine similarity matrices on vectors is generally known in the art and thus, a more detailed description is not provided herein. It should be appreciated that the illustrative embodiments are not limited to cosine similarity and may use any similarity evaluation algorithm that provides an indication of similarity between two vector representations, without departing from the spirit and scope of the present invention.

In addition, the temporal weighting engine 230 receives the vector representations 212 from the patient data vectorization engine 210 and generates a temporally weighted matrix T data structure 232, but with regard to temporal relatedness of different claim lines in the patient data. For example, the temporal weighting engine 230 may create a temporal weighting matrix T 232 such that $$T_{i,j} = \exp\left(\frac{-|\Delta t_{i,j}|}{T_c}\right),$$

where $\Delta t_{i,j}$ is the gap in time between service dates of the claims i and j and $T_c$ is a parameter to control the rate of decay.

The clustering engine 240 operates on the resulting matrices S and T (222 and 232) to cluster the medical concepts in the patient data 160 for the patient based on vector similarity and temporal weighting. The clustering performed by the clustering engine 240 may involve generating an affinity matrix A 242 as an element-wise product of the similarity matrix S 222 and the temporal weighting matrix T 232, i.e., A=S∘T. The clustering engine 240 further operates to perform affinity propagation clustering using the affinity matrix A. In this case, the entities that are the subject of the affinity matrix generation and affinity propagation are the claim lines, or claims, present in the similarity matrix S 222 and the temporal weighting matrix T 232, along with their corresponding medical concepts.

Thus, through the clustering, related claim lines or claims are identified. That is, the resulting clusters of claim lines or claims are used to define medical episodes. One or more clustering thresholds are used to define a degree of affinity needed to group or cluster claim lines or claims into the same group/cluster or medical episode. The clustering engine 240 evaluates cluster cohesion and filters out items with negative or low silhouette scores.

By identifying claim lines or claims as being in the same medical episode, medical episodes are defined for the patient, where the medical episode comprises all the medical concepts present in each of the included claim lines or claims. This process may be repeated for each patient in the input patient data 160 such that medical episodes for each patient are identified. These medical episodes for each patient may be stored in association with the patient's individual portion of the patient data 160 or otherwise associated with the patient such that the patient has their own associated set of medical episodes that were automatically identified via the medical episode pipeline 200. The medical episodes for each patient may be evaluated in this manner and stored as data structures which may then be analyzed by the medical episode definitions generator 250 to identify medical concepts related to a given anchor medical concept across a plurality of patients and their medical episodes involving that given anchor medical concept.

That is, given an anchor medical concept, such as a medical code for a medical condition or group/category associated with a medical condition, e.g., "diabetes", analysis of medical episodes that patients have which include this anchor medical concept may be identified and the frequency of occurrence of related medical concepts in these defined medical episodes may be evaluated across the various patients. Based on these frequencies of occurrence in medical episodes of patients, it can be determined which medical concepts are most likely to occur, in general, in association with the anchor medical concept in medical episodes. For example, a one or more frequency thresholds may be established that specifies one or more minimum frequencies needed to be considered sufficient to include in a general medical episode associated with the anchor medical concept as likely or not likely to be experienced by a patient for which the anchor medical concept is present. In other illustrative embodiments, a top N number of frequently occurring medical concepts in medical episodes having the anchor medical concept are selected to be part of a general medical episode definition for the anchor medical concept.

Based on this frequency evaluation, the resulting medical concepts identified across the various patients may be compiled into a general medical episode definition associated with the anchor medical concept. This can be done for various anchor medical concepts such that different medical episode definitions may be generated for different anchor medical concepts. These medical episode definitions may be stored in a medical episode definition storage 260, indexed by anchor medical concept for example, for later use in performing various types of evaluations.

For example, a user of a medical episode query system 270 may interface with the medical episode query system 270 to investigate medical episodes for various reasons, such as medical services cost projections, bundled payment analysis for determining a level of bundled payments to be provided for treatment of a particular medical condition, medical services scheduling, patient advising, etc. For example, by determining the definition of a medical episode in the manner described above, a user may access the medical episode definitions 260 via the medical episode query system 270 and input a search query for medical episodes associated with a particular medical concept of interest. The corresponding medical episodes may be retrieved and the medical episode definitions may be analyzed using reference data sets 170 to identify costs associated with the medical concepts in the medical episode definition with regard to medical services, treatments, medications, laboratory tests, annual doctor visits, etc., to generate an estimate of the costs to the medical insurance company and to the patient, the compensation provided to the medical professionals and medical facilities, etc.

In some illustrative embodiments, medical practitioners, clinicians, hospital administrators, medical practice managers, or the like, may utilize the medical episode query system 270 to obtain greater insights into medical episodes that may be associated with medical concepts for one or more of their patients. For example, for a patient associated with a given medical concept, e.g., a diagnosis or the like, by inputting the medical concept into the medical episode query system 270, the corresponding medical episode(s) associated with that medical concept may be retrieved from the medical episode definition storage 260 so that the user can determine what the patient can expect with regard to that medical concept, e.g., treatment of the medical condition corresponding to the medical diagnosis. For example, by viewing the content of a medical episode associated with a medical concept of interest, a clinician may be presented with a display of the medical services, procedures, treatments, prescriptions, etc., associated with the treatment of a medical condition corresponding to the medical concept of interest, along with cost estimates, bundled payment information, etc. For example, if the medical concept of interest is a knee replacement, the pre-op and post-op services, procedures, treatments, prescriptions, etc., that are part of the medical episode may be identified along with corresponding costs and other attributes, e.g., recovery times, likelihood of success, etc.

It should also be appreciated that the medical episodes identified by the clustering engine 240 for the individual patients may be stored in association with the patient data 160 for that patient such that it may be retrieved and used to evaluate individual patients. For example, a user of a medical episode query system 270 may access the medical episodes for an individual patient in order to provide a patient summary indicating the medical episodes associated with that particular patient. It should be appreciated that the medical concepts and claim lines, or claims, associated with a medical episode for the patient may be composed of medical concepts and/or claim lines or claims that may be from various disparate sources, e.g., different hospitals, medical professionals, medical practices, laboratories, clinics, pharmacies, etc. For example, a patient may be diagnosed at an urgent care clinic in Florida, to have bronchitis, sinusitis, and an ear infection and may be prescribed antibiotics. The same patient may later have an encounter with their primary care physician in Texas where the physician diagnoses the patient with a chronic cough and congestion and provide the patient with a steroid injection and a steroid inhaler. The patient may then return to the physician at a later time complaining of shortness of breath, and the physician may diagnose the patient with bronchitis and prescribe another antibiotic. All of these events, based on the analysis performed by the mechanisms of the illustrative embodiments, may be identified as correlating to the same medical episode and may be summarized by the mechanisms of the illustrative embodiments, e.g., a respiratory viral infection medical episode. The medical episode data structures associated with the patient data 160 for the patient will store the details of the instances of the claim lines or claims, including the medical concepts associated with those claim lines or claims associated with the medical episode, as extracted from the patient's medical information. This medical episode data structure may then be used as the basis for generating a summary of the medical episode, either by itself or as part of a plurality of medical episodes associated with the same patient, that may be presented to a user via a graphical user interface, for example, through which the user may drill-down into the details of the medical episode.

These medical episode summaries may be organized and presented to a user, e.g., medical professional, for assisting the user in understanding the medical condition of the patient in a concise and easy to access manner. The particular summaries may be generated based on a specification of the types of medical episodes that the user wishes to be informed of, e.g., the user may specify one or more medical concepts, e.g., medical conditions, or other criteria of a type of medical episode that the user is interested in viewing summary information about. The resulting graphical user interface (GUI) generated with the various summaries may be output to the user via their client computing device. The summaries in the GUI may be user selectable so as to implement a drill down capability. In this way, the user may select medical concept summaries or medical episode summaries and drill down into the particular sub-elements that contribute to the summary. Thus, the user may be presented a graphical user interface with the summaries corresponding to the user's specified interest, and may then select the summaries within the graphical user interface where the user wishes to see more detailed information about the medical episode.

Figure 3A:
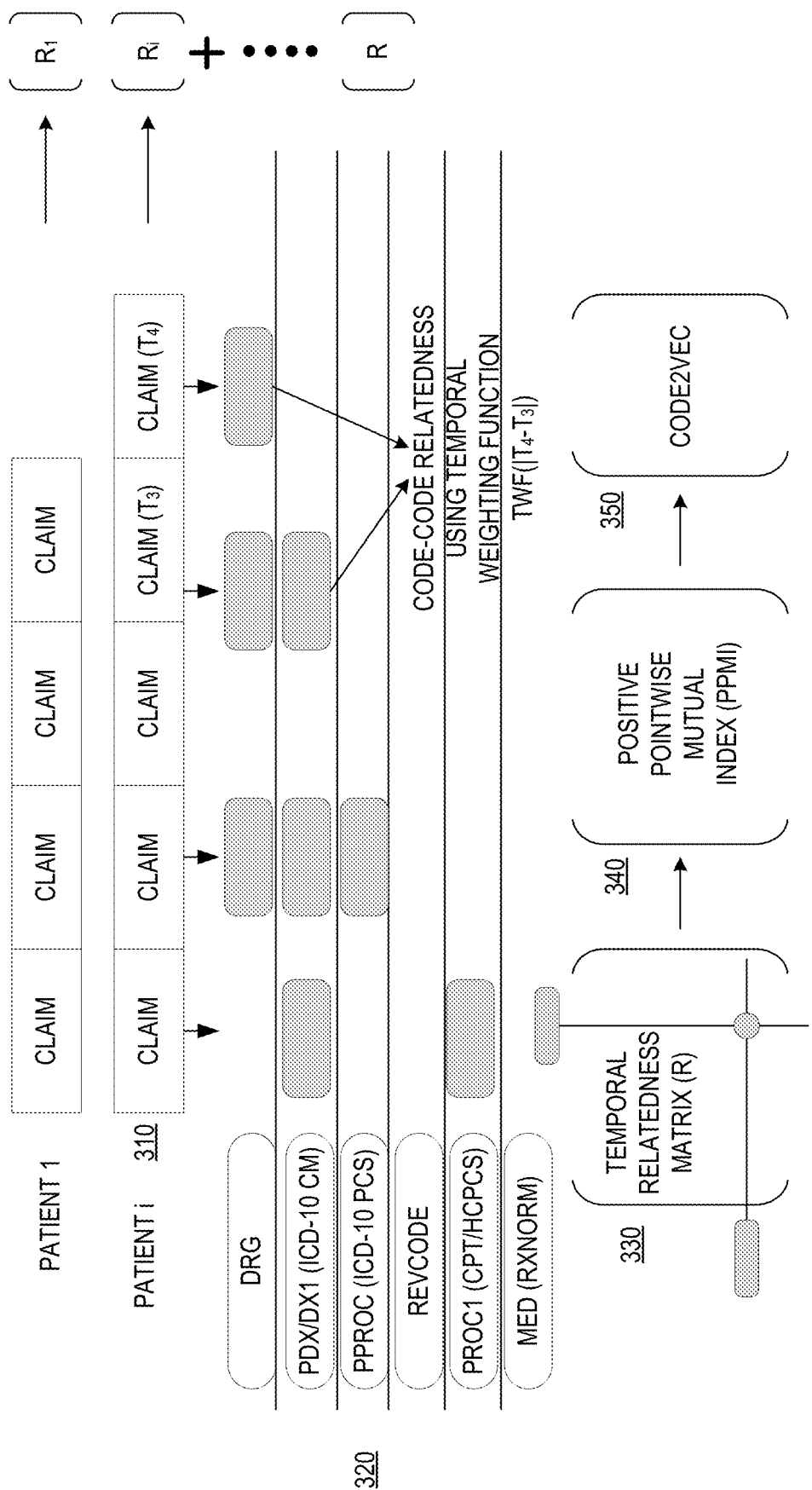
FIG. 3A is an example diagram illustrating an example embedding of a medical concept in accordance with one illustrative embodiment.

As discussed above, one aspect of the illustrative embodiments is the automatic learning of medical concept embeddings, such as through the mechanisms described above with regard to FIGS. 1A and 1B. FIG. 3A is an example diagram illustrating an example embedding of a medical concept in accordance with one illustrative embodiment. The example shown in FIG. 3A is for a medical concept embedding that is a medical code embedding from patient medical insurance claims data across a plurality of patients 1 to i, where claims data 310 is for patient i in the depicted example. Each patient 1 to i has a corresponding code-to-code temporally weighted relatedness matrix R1 to Ri generated through the operation of the illustrative embodiments, such as temporally weighted medical concept relatedness matrices 132.

As shown in FIG. 3A, a matrix 320 may be generated where claims in matrix are shown as columns with the corresponding medical concepts appearing in those claims being shaded boxes in corresponding rows associated with the medical concepts, e.g., DRG, PDX/DX1 (ICD-10 CM), PPROC (ICD-10PCS), REVCODE, etc. Each pairing of medical concepts present in claims for patient i in the patient claim data 310 will have a corresponding entry in the resulting temporally weighted relatedness matrix R 330 where the value in the entry, or cell, of the temporally weighted relatedness matrix R 330 is weighted based on the temporal distance between claims in which these medical concepts appear, e.g., a temporal weighting between medical concepts in the claim at time point t3 and medical concepts at time point t4 is a temporal weighting function (TWF) that is a function of the difference between t4 and t3. Thus, for example, the medical concept PDX/DX1 (ICD-10 CM) appears in combination with DRG twice in the example claims for patient i with the time points for the claims being t3 and t1 and thus, a value in the temporally weighted relatedness matrix R being the number of co-occurrences (2) weighted by a time weighted function of the difference in time points t3 and t1.

The resulting temporally weighted relatedness matrix R is then subjected to the relatedness metric calculation engine 140 which performs a positive point-wise mutual index (PPMI) evaluation to identify those entries where the co-occurrence of the medical concepts appears at a statistically significant frequency compared to the appearance of the medical concepts individually. The resulting statistically significant frequently occurring medical concept pairings are then provided to a vectorization engine 350 that converts the entries to vector representations, e.g., a code2vec operation.

Figure 3B:
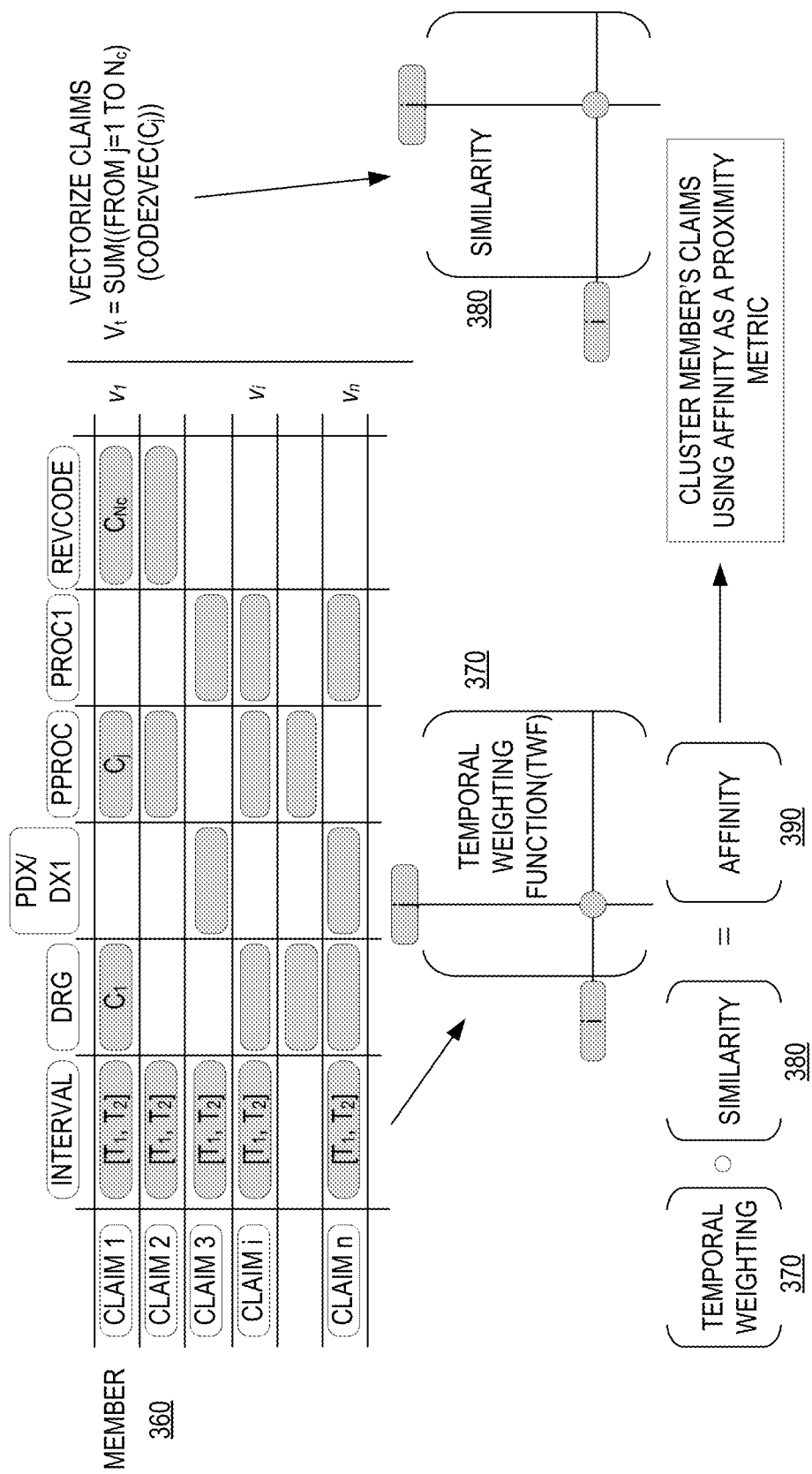
FIG. 3B is an example diagram illustrating an example operation for clustering a patient (or member) claims information into clusters representing medical episodes in accordance with one illustrative embodiment.

FIG. 3B is an example diagram illustrating an example operation for clustering a patient (or member) claims information into clusters representing medical episodes in accordance with one illustrative embodiment. As shown in FIG. 3B, a patient, or member (referring to the patient being a member of a health organization, such as a health insurance organization), has a plurality of claims (shown as rows in the matrix 360, where each claim has a corresponding interval, e.g., [t1, t2], and corresponding set of medical concepts, represented as shaded entries or cells, where columns in the matrix 360 correspond to different potential medical concepts that may be represented in the claims. The interval is used to generate a temporal weight using a temporal weight function (TWF) and a corresponding entry in the temporal weight matrix T 370 for each pairing of medical concepts $c_i$ and $c_j$. In addition, the vectorized claims data is used as a basis for generating a similarity matrix 380 indicating similarity measures between medical concepts, e.g., $c_i$ and $c_j$, such as by performing a cosine similarity analysis or the like. The temporal weight matrix T 370 is used along with the similarity matrix 380 to generate the affinity matrix 390 which is then the basis for clustering claims using affinity as the proximity metric. The resulting clusters are the medical episodes associated with the patient or member.

FIG. 4 is an example diagram illustrating a selection of a top-N number of medical concepts occurring in medical episodes of patients for generation of general medical episode definitions in accordance with one illustrative embodiment. In the depicted example, the value of N is configured to be 10 such that the top 10 frequently occurring medical concepts for medical episodes including corresponding anchor medical concepts are selected. It should be appreciated that any integer value for N may be selected that is desirable for the particular implementation. The medical concepts selected will be the ones that occur most frequently across medical episodes of a plurality of patients. Thus, for example, as shown in FIG. 4, for an anchor medical concept of "Osteoarthritis" the corresponding top 10 medical concepts 410 are selected. The medical concepts are listed with their corresponding descriptions being shown, but it can be appreciated that these selected medical concepts may in fact be medical codes which have these corresponding descriptions. The same is true for anchor medical concepts of "Ambulance Transportation", "Bariatric Surgery Procedures", and "Acute Myocardial Infarction" in the depicted example.

Thus, these top 10 medical concepts for each anchor medical concept may be used as a basis for generating a general medical episode definition for a medical episode corresponding to the anchor medical concept. For example, for osteoarthritis, a medical episode corresponding to osteoarthritis will likely involve: (1) an other aftercare encounter, (2) a major joint replacement or reattachment of a lower extremity, (3) anesthesia—knee and popliteal area, (4) surgical procedures on the femur (thigh region) and knee joint, (5) implant, device or graph related encounter—knee, (6) medical services—physical medicine and rehabilitation, (7) arthroplasty knee, (8) anesthesia—upper leg (except knee), (9) medical examination/evaluation, and (10) implant, device, or graph related encounter—hip. It should be appreciated that not all patients will experience medical episodes involving all 10 of these medical concepts. The medical episode definition identifies the most likely medical concepts associated with the anchor medical concept, as determined from analysis of a plurality of patients. It should also be appreciated that this medical episode definition is automatically generated from an analysis across a large set of different patients and potentially across a varied set of medical disciplines of various medical knowledge. Thus, an automated computing tool is provided that can automatically learn the medical concepts associated with medical episodes.

Figure 5A:
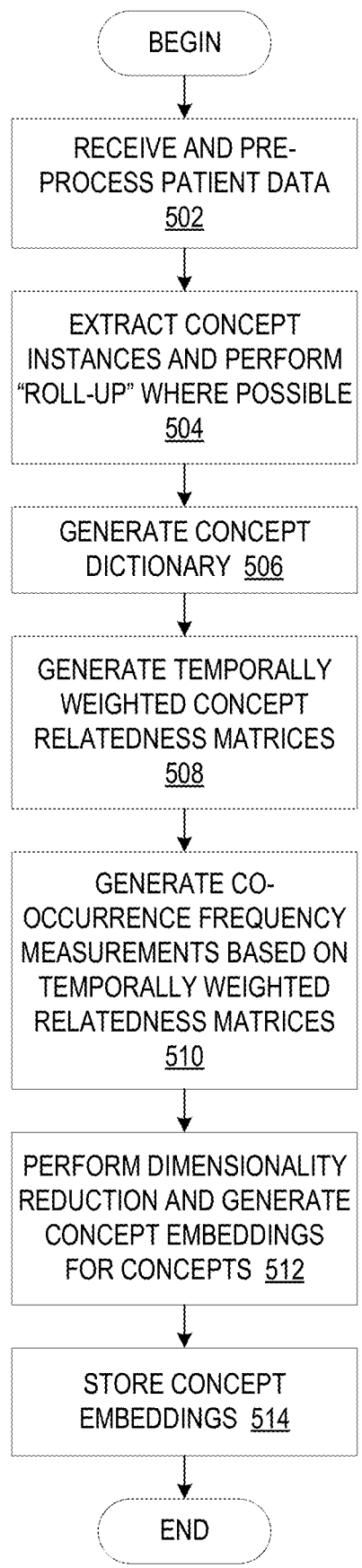
FIG. 5A is a flowchart outlining an example operation for automated machine learning based learning of medical concept embeddings in accordance with one illustrative embodiment.

FIG. 5A is a flowchart outlining an example operation for automated machine learning based learning of medical concept embeddings in accordance with one illustrative embodiment. The operation outlined in FIG. 5A may be performed, for example, by the medical concept embedding generation computer pipeline 100 in FIGS. 1A and 1B, for example. It should be appreciated that the operations outlined in the block diagrams of FIG. 5A are performed by one or more specifically configured computing devices that are specifically configured to perform these operations and thus, constitute special purpose computing device(s) of the medical concept embedding generation computer pipeline.

As shown in FIG. 5A, the operation starts with the receiving and pre-processing of patient data for automatically learning medical concept embeddings (step 502). The patient data is parsed and processed to extract instances of recognized medical concepts, recognized based on reference data set knowledge, and combine or "roll-up" instances of medical concepts into higher level group/category level medical concepts where appropriate (step 504). The resulting set of individual and group/category level medical concepts are used as a basis for generating a medical concept dictionary or vocabulary (step 506). The resulting set of individual and group/category level medical concepts are also used along with the medical concept dictionary/vocabulary to generate one or more temporally weighted medical concept relatedness matrices, each matrix having temporally weighted relatedness measures for pairings of medical concepts indicating how well the medical concepts are temporally related to one another as indicated in the identified instances of medical concepts extracted from the patient data (step 508). A measure of co-occurrence frequency is generated based on the temporally weighted medical concept relatedness matrices to generate one or more matrices indicating not only temporal relatedness but also co-occurrence frequency relatedness (step 510). The resulting matrices are processed through a dimensionality reduction operation to generate medical concept embeddings for each of the identified medical concepts, where the embeddings indicate the temporal and frequency relatedness of the medical concept to other recognized medical concepts (step 512). The medical concept embeddings are then stored for later use in generating vector representations of patient data (step 514). The operation then terminates.

Figure 5B:
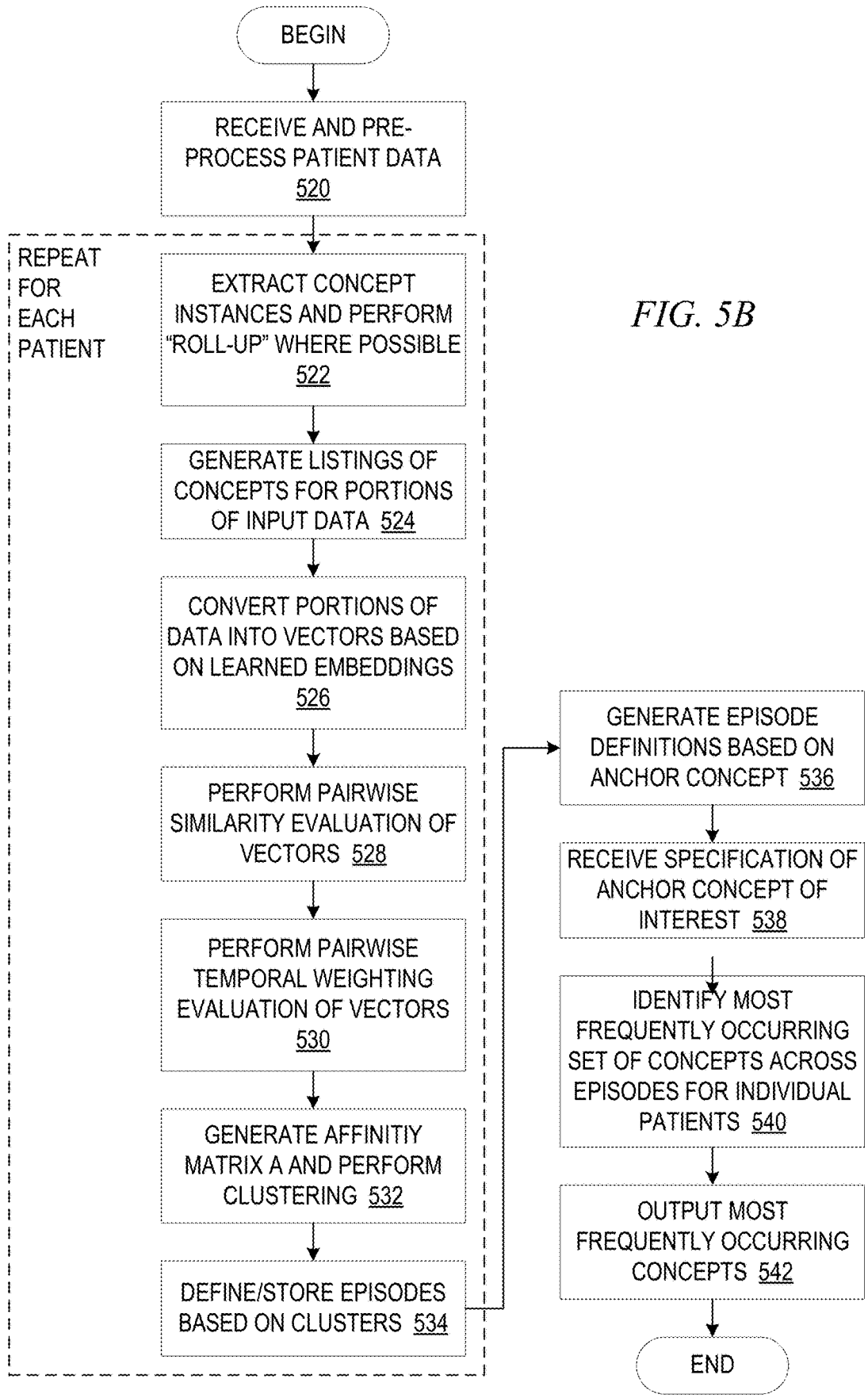
FIG. 5B is a flowchart outlining an example operation for automated medical episode definition generation in accordance with one illustrative embodiment.

FIG. 5B is a flowchart outlining an example operation for automated medical episode definition generation in accordance with one illustrative embodiment. The operation outlined in FIG. 5B may be performed, for example, by the medical episode definition generation computer pipeline 200 in FIGS. 2A and 2B, for example. It should be appreciated that the operations outlined in the block diagrams of FIG. 5A are performed by one or more specifically configured computing devices that are specifically configured to perform these operations and thus, constitute special purpose computing device(s) of the medical concept embedding generation computer pipeline.

As shown in FIG. 5B, the operation starts by receiving patient data for automatically generating medical episode definitions (step 520). The patient data may be organized into predefined portions of patient data, such as claim lines or claims, which may be processed on an individual patient basis. Thus, the subsequent operations outlined in FIG. 5B, i.e., steps 522-534, may be performed separate for each separate distinct patient in the patient data and then analysis of the resulting patient medical episodes may be performed across multiple patients to generate a more general medical episode definition based on an identification of a subset of medical concepts that are the most frequently occurring medical concepts in association with medical episodes having a specified anchor medical concept.

The patient data for a patient, organized into portions, such as claim lines or claims, is parsed and processed to extract instances of recognized medical concepts, recognized based on reference data set knowledge, and combine or "roll-up" instances of medical concepts into higher level group/category level medical concepts where appropriate (step 522). The resulting set of individual and group/category level medical concepts, still organized according to portions of patient data, are used as a basis for generating listings of identified medical concepts for each portion of patient data (step 524). The listings of identified medical concepts for each portion of patient data are then converted to vector representations of those portions of patient data, e.g., claim lines or claims, using the learned medical concept embeddings, such as from the operation of FIG. 5A (step 526).

The vector representations of the portions of patient data are used to perform a pairwise similarity evaluation between the vectors and generate a similarity matrix S (step 528). The vector representations of the portions of patient data are also used to perform a pairwise temporal weighting evaluation between the vectors and generate a temporal weighting matrix T (step 530). The similarity matrix S and temporal weighting matrix T are combined to generate an affinity matrix A that is used as a basis for clustering portions of patient data, e.g., clustering claim lines or claims (step 532). The resulting clusters are used to define patient medical episodes for the patient which may be stored in association with the patient's input data and for general medical episode definition generation across multiple patients (step 534). Again, this process may be repeated for each separate patient in the patient data.

Thereafter, the patient medical episode data may be used to generate general medical episode definitions based on the specification of one or more anchor medical concepts (step 536). For example, a medical concept, such as a medical condition, medical service, medical procedure, or the like, may be specified (step 538) as an anchor medical concept automatically or by a user via a user interface of a medical episode query computing system, and a cross-patient medical episode analysis is performed to identify a most frequently occurring set of medical concepts across medical episodes having the specified anchor medical concept (step 540). These most frequently occurring medical concepts may be output as the most likely medical concepts to occur in medical episodes involving the anchor medical concept (step 542). The operation then terminates.

Thus, the illustrative embodiments provide improved computing tools to automatically learn medical concept embeddings that specify the temporal and frequency based relatedness of medical concepts relative to other medical concepts. These automatically learned medical concept embeddings are then used to generate vector representations of portions of patient data, e.g., claim lines or claims, which are then evaluated for temporal closeness and vector similarity to cluster the portions of patient data and thereby identify patient medical episodes. The patient medical episodes across multiple patients may be evaluated to identify medical episode definitions for various anchor medical concepts. These medical episode definitions can then be used by other downstream computing systems to perform various decision making support operations including providing cost analysis, planning operations, scheduling operations, treatment recommendation operations, patient advising, and the like.

As is clear from the above description, the improved computing tool of the illustrative embodiments may be implemented through specific configuration of computing devices and/or data processing systems involving one or more specifically configured computing devices, of various data processing environments. In some illustrative embodiments, the data processing environment is a distributed data processing environment, such as a wide area network (WAN), local area network (LAN), the Internet, or the like, in which multiple computing devices operate in conjunction via one or more data networks and data network infrastructure devices, such as switches, routers, gateways, network attached storage devices, server computing devices, client computing devices, etc. which may facilitate wired and/or wireless data communication.

Figure 6:
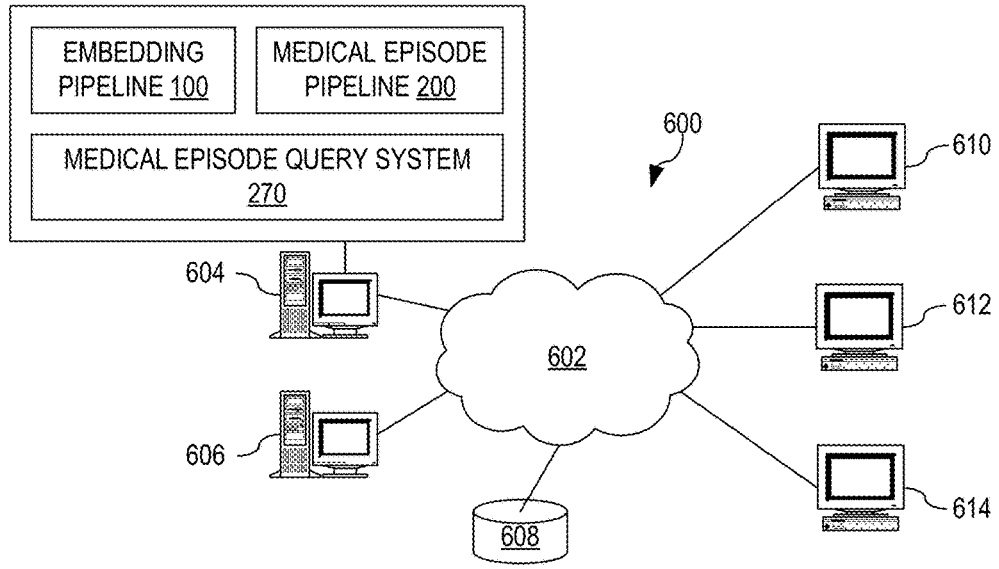
FIG. 6 is an example diagram of a distributed data processing system environment in which aspects of the illustrative embodiments may be implemented through specific configuration of computing devices to provide specific non-generic computing tools performing the operations and implementing the mechanisms of one or more of the illustrative embodiments.

FIG. 6 is an example diagram of a distributed data processing system environment in which aspects of the illustrative embodiments may be implemented through specific configuration of computing devices to provide specific non-generic computing tools performing the operations and implementing the mechanisms of one or more of the illustrative embodiments. Distributed data processing system 600 may include a network of computers in which aspects of the illustrative embodiments may be implemented. The distributed data processing system 600 contains at least one network 602, which is the medium used to provide communication links between various devices and computers connected together within distributed data processing system 600. The network 602 may include connections, such as wire, wireless communication links, or fiber optic cables.

In the depicted example, server 604 and server 606 are connected to network 602 along with storage unit 608. In addition, clients 610, 612, and 614 are also connected to network 602. These clients 610, 612, and 614 may be, for example, personal computers, network computers, or the like. In the depicted example, server 604 provides data, such as boot files, operating system images, and applications to the clients 610, 612, and 614. Clients 610, 612, and 614 are clients to server 604 in the depicted example. Distributed data processing system 600 may include additional servers, clients, and other devices not shown.

In the depicted example, distributed data processing system 600 is the Internet with network 602 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 600 may also be implemented to include a number of different types of networks, such as for example, an intranet, a local area network (LAN), a wide area network (WAN), or the like. As stated above, FIG. 6 is intended as an example, not as an architectural limitation for different embodiments of the present invention, and therefore, the particular elements shown in FIG. 6 should not be considered limiting with regard to the environments in which the illustrative embodiments of the present invention may be implemented.

As shown in FIG. 6, one or more of the computing devices, e.g., server 604, may be specifically configured to implement one or more of a medical concept embedding generation computer pipeline 100, a medical episode definition generation computer pipeline 200, and a medical episode query system 270. While FIG. 6 shows these elements being part of the same computing device, e.g., server 604, in other illustrative embodiments these elements 100, 200, and 270 may be distributed across a plurality of different server computing devices, and individual components of these elements 100, 200, and 270 may be distributed across multiple computing devices. However, whether in a single server computing device or distributed across multiple computing devices, each of these computing devices are specifically configured to implement corresponding components that implement the operations and functionality previously described above with regard to one or more illustrative embodiments. It should be appreciated that the configuring of the computing device(s) may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 604, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that a computing device is configured in one of these ways, the computing device becomes a specialized computing device, specifically configured to implement the mechanisms of the illustrative embodiments and is not a general purpose computing device. Moreover, as described herein, the implementation of the mechanisms of the illustrative embodiments improves the functionality of the computing device and provides a useful and concrete result that facilitates automated machine learning of medical concept embeddings detailing temporal and frequency of co-occurrence based relatedness of medical concepts, and automated identification of patient medical episodes and machine learning of medical episode definitions based on vectorization of patient data using the learned medical concept embeddings and clustering of vector representations of patient data into clusters corresponding to medical episodes.

For example, the server 604 may implement the medical concept embedding generation computer pipeline 100 to automatically learn medical concept embeddings from real-world patient data, which may be provided by a different computing system, or compiled from a plurality of different computing systems associated with different organizations that are sources of patient data, e.g., hospitals, medical practices, laboratories, clinics, pharmacies, etc. In some cases, the patient data may be obtained from a patient data warehouse computing system that itself compiles patient data from other source computing systems of these organizations. The automatically learning of these medical concept embeddings involves the evaluation of temporal weightings of medical concepts and frequency of co-occurrence of the medical concepts in portions of patient data, e.g., claim lines or claims. The same server 604, or another server on the network 602, may be configured to implement the medical episode definition generation computer pipeline 200 which may operate based on the medical concept embeddings and the patient data to identify medical episodes associated with individual patients and then perform a cross-patient medical episode analysis to identify general medical episode definitions for various anchor medical concepts.

Moreover, the same server 604, or another server on the network 602, may be configured to implement the medical episode query system 270 which may be facilitate user queries and/or other computing system automated queries, for medical episode information. For example, a clinician, hospital administrator, medical insurance company employee, or other user may log onto the medical episode query system 270 and may submit a query for information regarding medical episodes having a specified anchor medical concept. For example, a user may specify a particular medical condition, treatment, medical service, medical procedure, medication, or the like, for which medical episode information may be requested. This anchor medical concept may then be used to evaluate patient medical episodes and select a predetermined number of most frequently occurring medical concepts associated with patient medical episodes having the anchor medical concept. This listing of medical concepts may then be used to generate a general medical episode definition for the anchor medical concept, and the corresponding medical concept information for the general medical episode definition may be output to the user via a graphical user interface or the like.

Figure 7:
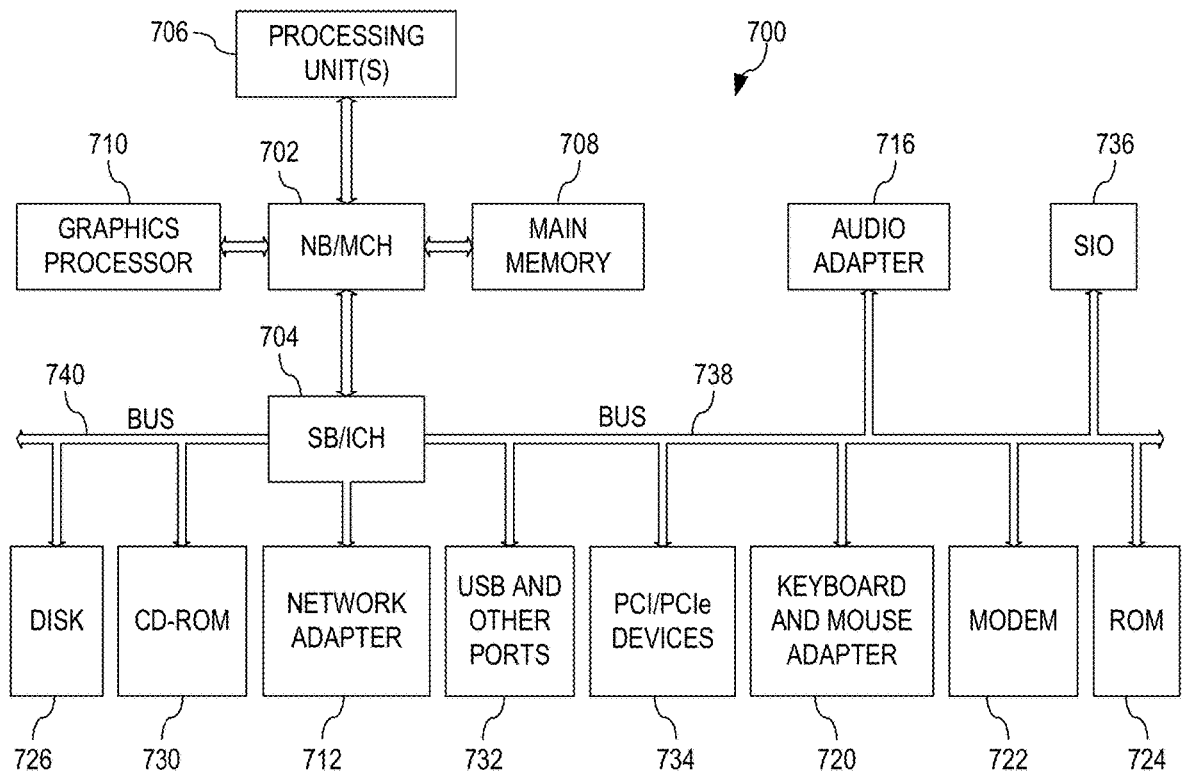
FIG. 7 is an example block diagram of a data processing system in which aspects of the illustrative embodiments may be implemented.

As noted above, the mechanisms of the illustrative embodiments utilize specifically configured computing devices, or data processing systems, to perform the operations for automatically learning, through machine learning processes, medical concept embeddings and using those medical concept embeddings to learn medical episode definitions. These computing devices, or data processing systems, may comprise various hardware elements which are specifically configured, either through hardware configuration, software configuration, or a combination of hardware and software configuration, to implement one or more of the systems/subsystems described herein. FIG. 7 is a block diagram of just one example data processing system in which aspects of the illustrative embodiments may be implemented. Data processing system 700 is an example of a computer, such as server 604 in FIG. 6, in which computer usable code or instructions implementing the processes and aspects of the illustrative embodiments of the present invention may be located and/or executed so as to achieve the operation, output, and external effects of the illustrative embodiments as described herein.

In the depicted example, data processing system 700 employs a hub architecture including north bridge and memory controller hub (NB/MCH) 702 and south bridge and input/output (I/O) controller hub (SB/ICH) 704. Processing unit 706, main memory 708, and graphics processor 710 are connected to NB/MCH 702. Graphics processor 710 may be connected to NB/MCH 702 through an accelerated graphics port (AGP).

In the depicted example, local area network (LAN) adapter 712 connects to SB/ICH 704. Audio adapter 716, keyboard and mouse adapter 720, modem 722, read only memory (ROM) 724, hard disk drive (HDD) 726, CD-ROM drive 730, universal serial bus (USB) ports and other communication ports 732, and PCI/PCIe devices 734 connect to SB/ICH 704 through bus 738 and bus 740. PCI/PCIe devices may include, for example, Ethernet adapters, add-in cards, and PC cards for notebook computers. PCI uses a card bus controller, while PCIe does not. ROM 724 may be, for example, a flash basic input/output system (BIOS).

HDD 726 and CD-ROM drive 730 connect to SB/ICH 704 through bus 740. HDD 726 and CD-ROM drive 730 may use, for example, an integrated drive electronics (IDE) or serial advanced technology attachment (SATA) interface. Super I/O (SIO) device 736 may be connected to SB/ICH 704.

An operating system runs on processing unit 706. The operating system coordinates and provides control of various components within the data processing system 700 in FIG. 7. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 700.

As a server, data processing system 700 may be, for example, an IBM eServer™ System P® computer system, Power™ processor based computer system, or the like, running the Advanced Interactive Executive (AIX®) operating system or the LINUX® operating system. Data processing system 700 may be a symmetric multiprocessor (SMP) system including a plurality of processors in processing unit 706. Alternatively, a single processor system may be employed.

Instructions for the operating system, the object-oriented programming system, and applications or programs are located on storage devices, such as HDD 726, and may be loaded into main memory 708 for execution by processing unit 706. The processes for illustrative embodiments of the present invention may be performed by processing unit 706 using computer usable program code, which may be located in a memory such as, for example, main memory 708, ROM 724, or in one or more peripheral devices 726 and 730, for example.

A bus system, such as bus 738 or bus 740 as shown in FIG. 7, may be comprised of one or more buses. Of course, the bus system may be implemented using any type of communication fabric or architecture that provides for a transfer of data between different components or devices attached to the fabric or architecture. A communication unit, such as modem 722 or network adapter 712 of FIG. 7, may include one or more devices used to transmit and receive data. A memory may be, for example, main memory 708, ROM 724, or a cache such as found in NB/MCH 702 in FIG. 7.

As mentioned above, in some illustrative embodiments the mechanisms of the illustrative embodiments may be implemented as application specific hardware, firmware, or the like, application software stored in a storage device, such as HDD 726 and loaded into memory, such as main memory 708, for executed by one or more hardware processors, such as processing unit 706, or the like. As such, the computing device shown in FIG. 7 becomes specifically configured to implement the mechanisms of the illustrative embodiments and specifically configured to perform the operations and generate the outputs described herein with regard to the pipelines 100 and 200, and potentially the query system 270.

Those of ordinary skill in the art will appreciate that the hardware in FIGS. 6 and 7 may vary depending on the implementation. Other internal hardware or peripheral devices, such as flash memory, equivalent non-volatile memory, or optical disk drives and the like, may be used in addition to or in place of the hardware depicted in FIGS. 6 and 7. Also, the processes of the illustrative embodiments may be applied to a multiprocessor data processing system, other than the SMP system mentioned previously, without departing from the spirit and scope of the present invention.

Moreover, the data processing system 700 may take the form of any of a number of different data processing systems including client computing devices, server computing devices, a tablet computer, laptop computer, telephone or other communication device, a personal digital assistant (PDA), or the like. In some illustrative examples, data processing system 700 may be a portable computing device that is configured with flash memory to provide non-volatile memory for storing operating system files and/or user-generated data, for example. Essentially, data processing system 700 may be any known or later developed data processing system without architectural limitation.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to configure the at least one processor to implement an automated episode generation pipeline that operates to perform the method comprising:

generating a first matrix data structure, comprising a temporally weighted concept relatedness matrix, based on temporal characteristics of concept instances in a plurality of concept instances extracted from input data, wherein the first matrix data structure comprises an entry for each pair of concepts identified in the plurality of concept instances, and wherein the entry stores a value representing a base level of relatedness of the corresponding concepts in the corresponding pair of concepts, weighted according to a temporal weighting function and temporal characteristics of the concept instances of the corresponding concepts;

generating, by processing the first matrix data structure, a second matrix data structure, comprising a temporally weighted co-occurrence frequency correlated relatedness matrix, wherein the second matrix data structure comprises, for each entry in the first matrix data structure, a measure of a relatedness of the corresponding concepts in the pair of concepts based on a frequency of occurrence, of the concepts in the pair of concepts, occurring together in the input data;

generating, for each first concept in the plurality of concept instances, a concept embedding data structure based on the second matrix data structure, wherein the concept embedding data structure specifies, for each other second concept, a measure of temporally weighted relatedness of the first concept with the second concept;

generating, for each of one or more anchor concepts, a corresponding episode definition data structure comprising a plurality of related concepts corresponding to a same episode, based on the concept embedding data structures, to thereby generate one or more episode definition data structures; and processing new input data based on the one or more episode definition data structures to identify instances of corresponding one or more episodes in the new input data.

2. The method of claim 1, wherein generating the second matrix data structure comprises executing a positive pointwise mutual information (PPMI) analysis of the entries in the first matrix data structure.

3. The method of claim 1, wherein the concept embedding data structure is a multi-dimensional vector space representation of second concepts occurring in combination with the first concept weighted according to a temporal distance between occurrences of the first concept with the second concepts, where weights are relatively greater for smaller temporal distances than for longer temporal distances.

4. The method of claim 1, wherein generating the episode definition data structure comprises:

performing a clustering operation on the embedding data structures based on a pairwise vector similarity and pairwise temporal weighting to generate a plurality of clusters; and generating an episode definition data structure for each cluster in the plurality of clusters based on a group of embedding data structures corresponding to the cluster.

5. The method of claim 4, wherein the input data is patient EMR data, the episodes are medical episodes corresponding to a medical condition, and the group of embedding data structures corresponding to a cluster that corresponds to the episode definition data structure includes medical concepts across a plurality of medical disciplines.

6. The method of claim 1, wherein the input data is real-world patient electronic medical record (EMR) data for a plurality of patients in a consolidated patient EMR data repository that gathers patient EMR data from a plurality of different source computing systems.

7. The method of claim 6, further comprising:

processing the real-world patient EMR data to extract the concepts from the real-world patient EMR data, wherein the concepts are medical concepts corresponding to at least one of medical conditions, treatments for the medical conditions, medical services associated with the medical conditions, laboratory results corresponding to the medical conditions, or medications corresponding to the medical conditions; and combining instances of medical concepts associated with a same higher level medical concept in an ontology data structure into the higher-level medical concept.

8. The method of claim 7, wherein the medical concepts are medical codes present in the real-world patient EMR data.

9. The method of claim 1, wherein the new input data is patient electronic medical record (EMR) data, and wherein processing the new input data based on the one or more episode definition data structures to identify instances of corresponding one or more episodes in the new input data comprises:
   evaluating the patient EMR data to identify medical episodes present in the patient EMR data based on matching data in the patient EMR data to one or more elements of the one or more episode definition data structures; and
   generating an episode summary output identifying each of the identified medical episodes.

10. The method of claim 1, wherein the new input data is patient electronic medical record (EMR) data, and wherein the new input data based on the one or more episode definition data structures to identify instances of corresponding one or more episodes in the new input data comprises:
   evaluating, for an anchor medical condition, patient EMR data for a plurality of patients to identify medical episodes corresponding to the anchor medical condition based on matching data in the patient EMR data to one or more elements of the one or more episode definition data structures; and
   generating a medical episode output specifying frequently occurring elements of medical episodes, corresponding to the anchor medical condition, across the plurality of patients.

11. A computer program product comprising a computer readable storage medium having a computer readable program stored therein, wherein the computer readable program, when executed on a data processing system, causes the data processing system to implement an automated episode generation pipeline that operates to:
   generate a first matrix data structure, comprising a temporally weighted concept relatedness matrix, based on temporal characteristics of concept instances in a plurality of concept instances extracted from input data, wherein the first matrix data structure comprises an entry for each pair of concepts identified in the plurality of concept instances, and wherein the entry stores a value representing a base level of relatedness of the corresponding concepts in the corresponding pair of concepts, weighted according to a temporal weighting function and temporal characteristics of the concept instances of the corresponding concepts;
   generate, by processing the first matrix data structure, a second matrix data structure, comprising a temporally weighted co-occurrence frequency correlated relatedness matrix, wherein the second matrix data structure comprises, for each entry in the first matrix data structure, a measure of a relatedness of the corresponding concepts in the pair of concepts based on a frequency of occurrence, of the concepts in the pair of concepts, occurring together in the input data;
   generate, for each first concept in the plurality of concept instances, a concept embedding data structure based on the second matrix data structure, wherein the concept embedding data structure specifies, for each other second concept, a measure of temporally weighted relatedness of the first concept with the second concept;
   generate, for each of one or more anchor concepts, a corresponding episode definition data structure comprising a plurality of related concepts corresponding to a same episode, based on the concept embedding data structures, to thereby generate one or more episode definition data structures; and
   process new input data based on the one or more episode definition data structures to identify instances of corresponding one or more episodes in the new input data.

12. The computer program product of claim 11, wherein generating the second matrix data structure comprises executing a positive point-wise mutual information (PPMI) analysis of the entries in the first matrix data structure.

13. The computer program product of claim 11, wherein the concept embedding data structure is a multi-dimensional vector space representation of second concepts occurring in combination with the first concept weighted according to a temporal distance between occurrences of the first concept with the second concepts, where weights are relatively greater for smaller temporal distances than for longer temporal distances.

14. The computer program product of claim 11, wherein generating the episode definition data structure comprises:
   performing a clustering operation on the embedding data structures based on a pairwise vector similarity and pairwise temporal weighting to generate a plurality of clusters; and
   generating an episode definition data structure for each cluster in the plurality of clusters based on a group of embedding data structures corresponding to the cluster.

15. The computer program product of claim 14, wherein the input data is patient EMR data, the episodes are medical episodes corresponding to a medical condition, and the group of embedding data structures corresponding to a cluster that corresponds to the episode definition data structure includes medical concepts across a plurality of medical disciplines.

16. The computer program product of claim 11, wherein the input data is real-world patient electronic medical record (EMR) data for a plurality of patients in a consolidated patient EMR data repository that gathers patient EMR data from a plurality of different source computing systems.

17. The computer program product of claim 16, wherein the computer readable program further causes the data processing system to:
   process the real-world patient EMR data to extract the concepts from the real-world patient EMR data, wherein the concepts are medical concepts corresponding to at least one of medical conditions, treatments for the medical conditions, medical services associated with the medical conditions, laboratory results corresponding to the medical conditions, or medications corresponding to the medical conditions; and
   combine instances of medical concepts associated with a same higher level medical concept in an ontology data structure into the higher-level medical concept.

18. The computer program product of claim 11, wherein the new input data is patient electronic medical record (EMR) data, and wherein processing the new input data based on the one or more episode definition data structures to identify instances of corresponding one or more episodes in the new input data comprises:

evaluating the patient EMR data to identify medical episodes present in the patient EMR data based on matching data in the patient EMR data to one or more elements of the one or more episode definition data structures; and generating an episode summary output identifying each of the identified medical episodes.

19. The computer program product of claim 11, wherein the new input data is patient electronic medical record (EMR) data, and wherein the new input data based on the one or more episode definition data structures to identify instances of corresponding one or more episodes in the new input data comprises:

evaluating, for an anchor medical condition, patient EMR data for a plurality of patients to identify medical episodes corresponding to the anchor medical condition based on matching data in the patient EMR data to one or more elements of the one or more episode definition data structures; and generating a medical episode output specifying frequently occurring elements of medical episodes, corresponding to the anchor medical condition, across the plurality of patients.

20. An apparatus comprising:

at least one processor; and at least one memory coupled to the processor, wherein the at least one memory comprises instructions which, when executed by the at least one processor, cause the at least one processor to implement an automated episode generation pipeline that operates to:

generate a first matrix data structure, comprising a temporally weighted concept relatedness matrix, based on temporal characteristics of concept instances in a plurality of concept instances extracted from input data, wherein the first matrix data structure comprises an entry for each pair of concepts identified in the plurality of concept instances, and wherein the entry stores a value representing a base level of relatedness of the corresponding concepts in the corresponding pair of concepts, weighted according to a temporal weighting function and temporal characteristics of the concept instances of the corresponding concepts;

generate, by processing the first matrix data structure, a second matrix data structure, comprising a temporally weighted co-occurrence frequency correlated relatedness matrix, wherein the second matrix data structure comprises, for each entry in the first matrix data structure, a measure of a relatedness of the corresponding concepts in the pair of concepts based on a frequency of occurrence, of the concepts in the pair of concepts, occurring together in the input data;

generate, for each first concept in the plurality of concept instances, a concept embedding data structure based on the second matrix data structure, wherein the concept embedding data structure specifies, for each other second concept, a measure of temporally weighted relatedness of the first concept with the second concept;

generate, for each of one or more anchor concepts, a corresponding episode definition data structure comprising a plurality of related concepts corresponding to a same episode, based on the concept embedding data structures, to thereby generate one or more episode definition data structures; and process new input data based on the one or more episode definition data structures to identify instances of corresponding one or more episodes in the new input data.

* * * * *